(12) United States Patent
Barclay et al.

(10) Patent No.: US 7,862,522 B1
(45) Date of Patent: Jan. 4, 2011

(54) SENSOR GLOVE

(75) Inventors: David Barclay, 312 S. Keystone St., Burbank, CA (US) 91506; Glenn Silver, Montreal (CA); Johan Versteegh, Dieren (NL); Bruce Lanoil, Valencia, CA (US)

(73) Assignee: David Barclay, Burbank, CA (US)

( * ) Notice: Subject to any disclaimer, the term of this patent is extended or adjusted under 35 U.S.C. 154(b) by 1167 days.

(21) Appl. No.: 11/501,547

(22) Filed: Aug. 8, 2006

Related U.S. Application Data

(60) Provisional application No. 60/706,627, filed on Aug. 8, 2005.

(51) Int. Cl.
*A61B 5/103* (2006.01)
*A61B 5/117* (2006.01)
*A61H 1/00* (2006.01)
*A61H 1/02* (2006.01)
*A61H 5/00* (2006.01)
*B25J 1/00* (2006.01)
*B25J 3/00* (2006.01)
*B25J 15/00* (2006.01)
*B25J 19/00* (2006.01)
*B25J 3/04* (2006.01)
*B25J 13/08* (2006.01)

(52) U.S. Cl. ............... 600/595; 600/587; 601/33; 601/40; 414/2; 414/3; 414/4; 414/5; 414/6; 414/7

(58) Field of Classification Search ............... 600/595; 73/379.01–379.03, 865.4; 601/33, 40; 33/512; 482/44, 47; 623/57, 64; 901/1–18; 414/2–7
See application file for complete search history.

(56) References Cited

U.S. PATENT DOCUMENTS

| | | | | |
|---|---|---|---|---|
| 5,354,162 | A | * | 10/1994 | Burdea et al. .............. 414/5 |
| 5,683,351 | A | * | 11/1997 | Kaiser et al. .............. 601/40 |
| 2002/0198472 | A1 | * | 12/2002 | Kramer .................. 600/595 |

* cited by examiner

*Primary Examiner*—Max Hindenburg
*Assistant Examiner*—Devin Henson
(74) *Attorney, Agent, or Firm*—James F. Kirk

(57) ABSTRACT

A Sensor glove is an instrument, in the same way that a piano is an instrument. The Sensor glove is purchased and the owner then learns to use it and the sensors therein to develop the performance of a sound, character or model, or to "conduct" or "play" the sensor movements and experience the response of the model in real time. Several performers with a number of the Sensor glove can control over 200 motors or hundreds of control points on a character at one time, manipulate audio data, or computer images etc. The characteristics of the sensors on the gloves can be adjusted to the needs and demands of the wearer or the many performer and wearers in those venues where multiple performers are used with many gloves to control or produce the motions and sounds of many distinct characters in a screen play.

8 Claims, 23 Drawing Sheets

Molded Nylon 14-1/2 deg angle spur gear
48 pitch, 1/8" bore
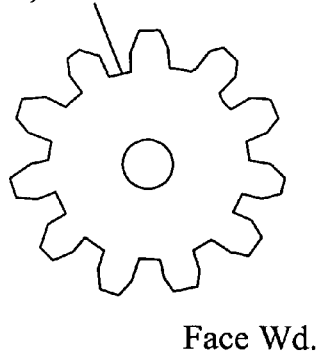
Face Wd.
FIG. 12a
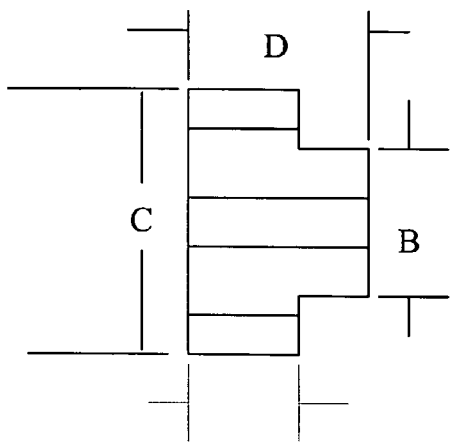
FIG. 12b
TABLE 1
| Teeth | Pitch Diam (A) | Hub Diam (B) | OD (C) | O'all Lg (D) |
|---|---|---|---|---|
| 44 | 0.917" | 9/32" | 0.95" | 3/8" |
| 24 | 0.5" | 3/8" | 0.54" | 3/8" |
| 16 | 0.333" | 1/4" | 0.37" | 5/16" |
FIG. 12c

SENSOR GLOVE

This non-provisional application claims priority from Provisional Patent Application Ser. No. 60/706,627 filed Aug. 8, 2005 for a Sensor Glove and having common inventors and assignees.

FIELD OF THE INVENTION

Motion Control and Animation—primary markets; film and television production, computer game industry, motion capture. An input device designed to allow the user direct interface via a computer with a real time tactile experience, i.e. joysticks, face-tracking headsets. A hand covering in the form of a glove, and used for the control of motion, sound and light.

BACKGROUND OF THE INVENTION

First sensor glove was created in 1991, using potentiometers, for the animatronic company Ultimate Animates, based in Hertfordshire, England. The gloves were used for controlling animatronic servo motors such as those used in connection with puppet characters that appeared in movies and for the TV industry. The inventor of the first gloves used at that time was common with and to this invention, inventor Dave Barclay.

Various versions of the glove were developed during the 1990's, all using potentiometers. Bulky wiring, and a limited application for the analogue output of potentiometers limited the early application of the gloves in service, and because of high maintenance requirements.

Technology Playgroup of Montreal, Canada was commissioned by Dave Barclay in 1996 to assist in the development of the "Barclaybox". The Barclaybox was designed to convert the analogue signals from potentiometers into digital signals which were read by a Silicon Graphics Indigo 2 Extreme computer, running Softimage 3 software. The combination allowed real time movement and control of 3D computer graphic models directly from the glove. Glenn Silver led the development of the Barclaybox.

The Sensor glove allows the wearer of the a unique ability to "play" the dynamic movements generated by the sensors in a manner comparable to that in which a musician playing a musical instrument. The use of a glove to produce the motion of a cartoon character or a puppet that is achieved in real time is referred to as "tuned" when the outputs of the sensor glove are calibrated or modeled to each user's preferences.

Auxiliary Anatomical Reference

U.S. Pat. No. 7,000,253 which issued to James M. Kleinert on Feb. 21, 2006 provided a schematic in its FIG. 2, showing an anatomical view of the bones of a right human hand 310. FIG. 2 from the 253 reference is the basis for FIG. 13 shown herein. The six paragraphs that appear in the '253' reference that explain Kleinert's FIG. 2 are copied and quoted herein verbatim for the convenience of the reader as an added reference and to assist in characterizing the location of components of the subject invention sensor glove with respect to the location of the anatomical features of the human hand.

From The '253' Reference:

FIG. 13 (FIG. 2) "is a schematic anatomical view of the bones of a right human hand 310 looking at a dorsal side. Shown are the radius 320, ulna 321, radiocarpal joint (RC) 323', distal radio ulnar joint (DRUJ) 322, wrist 312, thumb 364, index finger 365, long finger 366, ring finger 367, and small finger 368. Also shown is a carpus 369 which comprises eight carpal bones, seven of which are shown in FIG. 2. This includes the hamate bone 371 with its hook-like protrusion, the scaphoid 324', the lunate 325 and the triquetrum 373.

The thumb 364 is comprised of the distal phalanx 351, the interphalangeal joint (IP) 346, proximal phalanx 341, diaphysis proximal phalanx 341', metacarpalphalangeal joint (MCP) 336, metacarpal 331, and carpometacarpal joint (CMC) 326.

The index finger 365 is comprised of the distal phalanx 360, distal interphalangeal joint (DIP) 356, middle phalanx 352, proximal interphalangeal joint (PIP) 347, proximal phalanx 342, metacarpalphalangeal joint (MCP) 337, metacarpal 332, and carpometacarpal joint (CMC) 327.

The long finger 366 is comprised of the distal phalanx 361 distal interphalangeal joint (DIP) 357, middle phalanx 353, proximal interphalangeal joint (PIP) 348, proximal phalanx 343, metacarpalphalangeal joint (MCP) 338, metacarpal 333, and carpometacarpal joint (CMC) 323.

The ring finger 367 is comprised of the distal phalanx 362, distal interphalangeal joint (DIP) 358, middle phalanx 354, proximal interphalangeal joint (PIP) 349, proximal phalanx 344, metacarpalphalangeal joint (MCP) 339, metacarpal 334, and carpometacarpal joint (CMC) 324.

The small finger 368 is comprised of the distal phalanx 363, distal interphalangeal joint (DIP) 359, middle phalanx 355, proximal interphalangeal joint (PIP) 350, proximal phalanx 345, metacarpalphalangeal joint (MCP) 340, metacarpal 335, and carpometacarpal joint (CMC) 330."

SUMMARY OF THE INVENTION

A combination of potentiometers and flex sensors are mounted on a flexible fabric base coupled to a reference unit, to generate signals in response to the movement or articulation of a hand or individual fingers or joints that are in contact with the fabric, resulting in an organic composite movement for creating performances in motion, sound and light, in response to the movement of the fingers and hand within the glove worn by an artist, a performer or a puppeteer with the skill necessary to produce an animated performance for viewing in and for film or video media. The performer uses the transducer like a musician playing a musical instrument.

Additional Force Sensing Resistors, and Accelerometers are combined on the sensor glove to provide a repetitive sequence of arrays of sampled data that is used to characterize the movement and or the performance of a character such as a puppet or an image, as in a cartoon character, that is appearing in a screen play performance or in the modeled performance of a robot or puppet. The "tunable" dynamic movement data, along with data from potentiometers and flex sensors is filtered and converted to digital signals by the on-board circuitry and electronics ("SBsmart") The data produced is then digitally processed. The data is prepared for transmission and then sent via a proprietary RS-485 serial data bus (referred to as "SBbus") to the Sensorbox Communications Unit (referred to as "KoRe"), which manages and directs data from a plurality of PerformFX or Sensor gloves and other wired or wireless Sensorbox KoRes into various computers using an RS 232, a serial or a USB buss, an Ethernet, and or a CAN (Controller Area Network) bus or protocol.

The sensors on the glove discern motion and generate signals that provide a simulation of the motion. The signals provided are characterized as dynamic movement or motion signals. The signals are used to control motor drives, hydraulics, servos, pneumatics, computer images, sound files, musical instruments and computer controlled lights in an organic or fluid manner.

A BRIEF DESCRIPTION OF THE DRAWINGS

FIG. 12a and FIG. 12b are respective front and side views of a spur gear of a type used to couple and scale mechanical motion to the potentiometers used on the sensor glove;

FIG. 12c is a Table that identifies the mechanical features of the spur gears of FIGS. 12a and 12b;

DESCRIPTION OF PREFERRED EMBODIMENT

Figure 1:
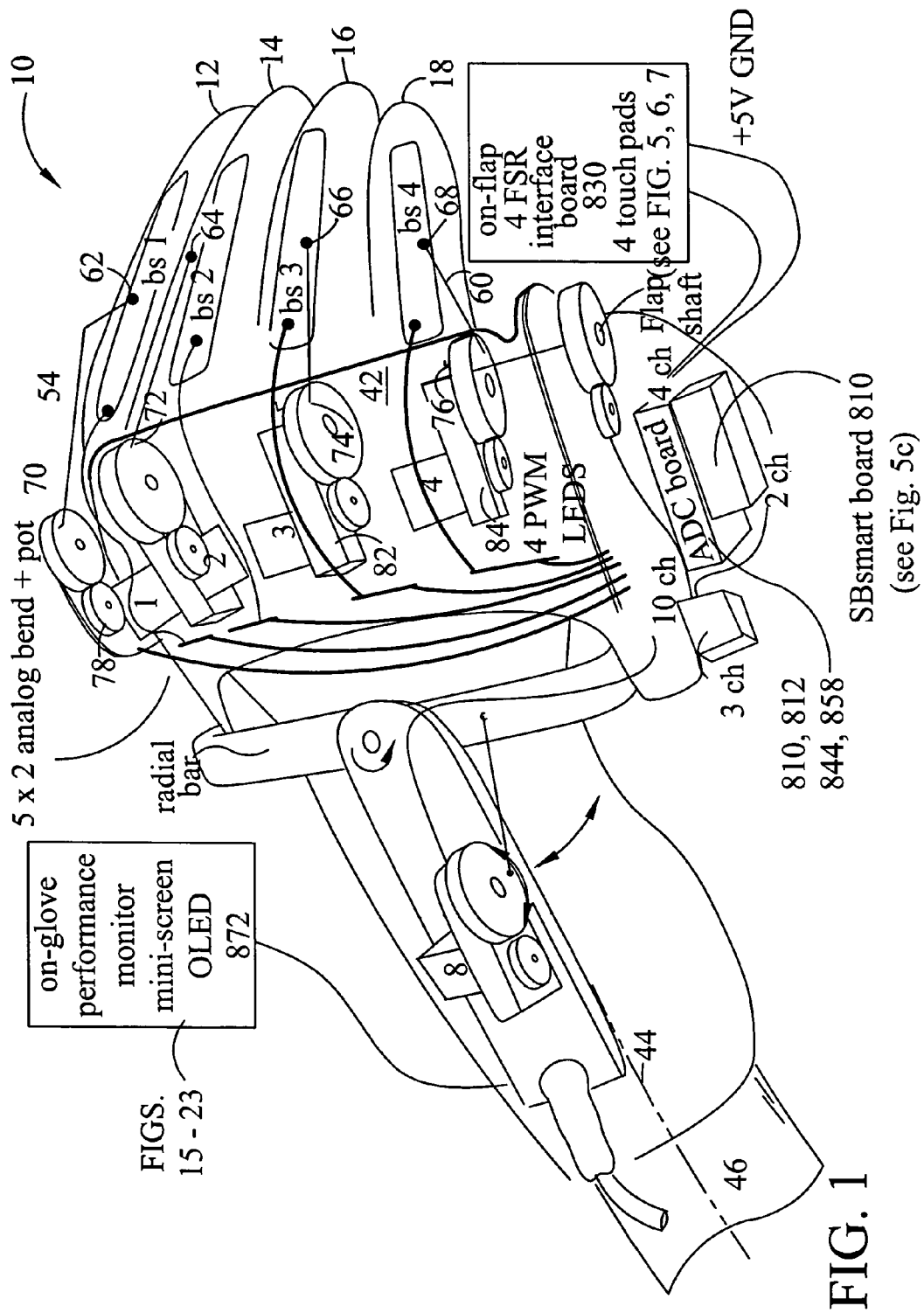
FIG. 1 is a dorsal side back to-front (wrist to finger) perspective view of the sensor gloves showing the ADC board stacked under the ABsmart signal conditioning board

FIG. 1 shows the sensor glove 10 in a perspective view as it is worn on the fingers and hand of a performer (not shown). The sensor glove 10 is used to provide signals representing the motion of one or more fingers, shown generally as 12, 14, 16, 18 and a thumb, (not shown) in relation to the rigid reference base 42.

Figure 2:
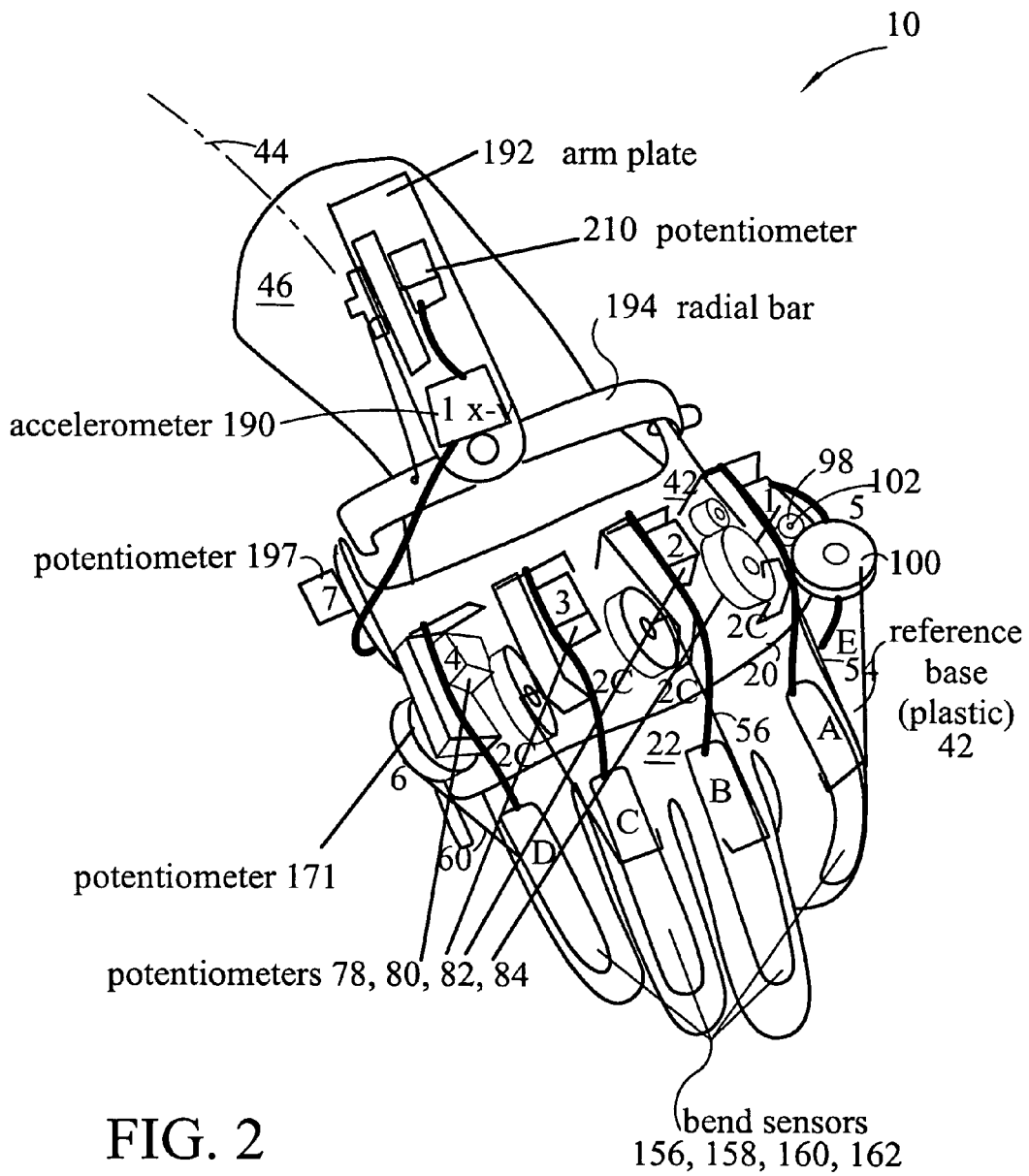
FIG. 2 is a dorsal side front-to-back (finger to wrist) perspective view of the sensor glove, labeled with key component descriptions.

FIG. 2 shows the rigid reference base 42 coupled to the top or dorsal surface of the palmer region 22 of the sensor glove 10. The sensor glove 10 has a palmer region shown within the limits of a bracket 26, shown on FIG. 13 and discussed above in connection with the Background.

Figure 3:
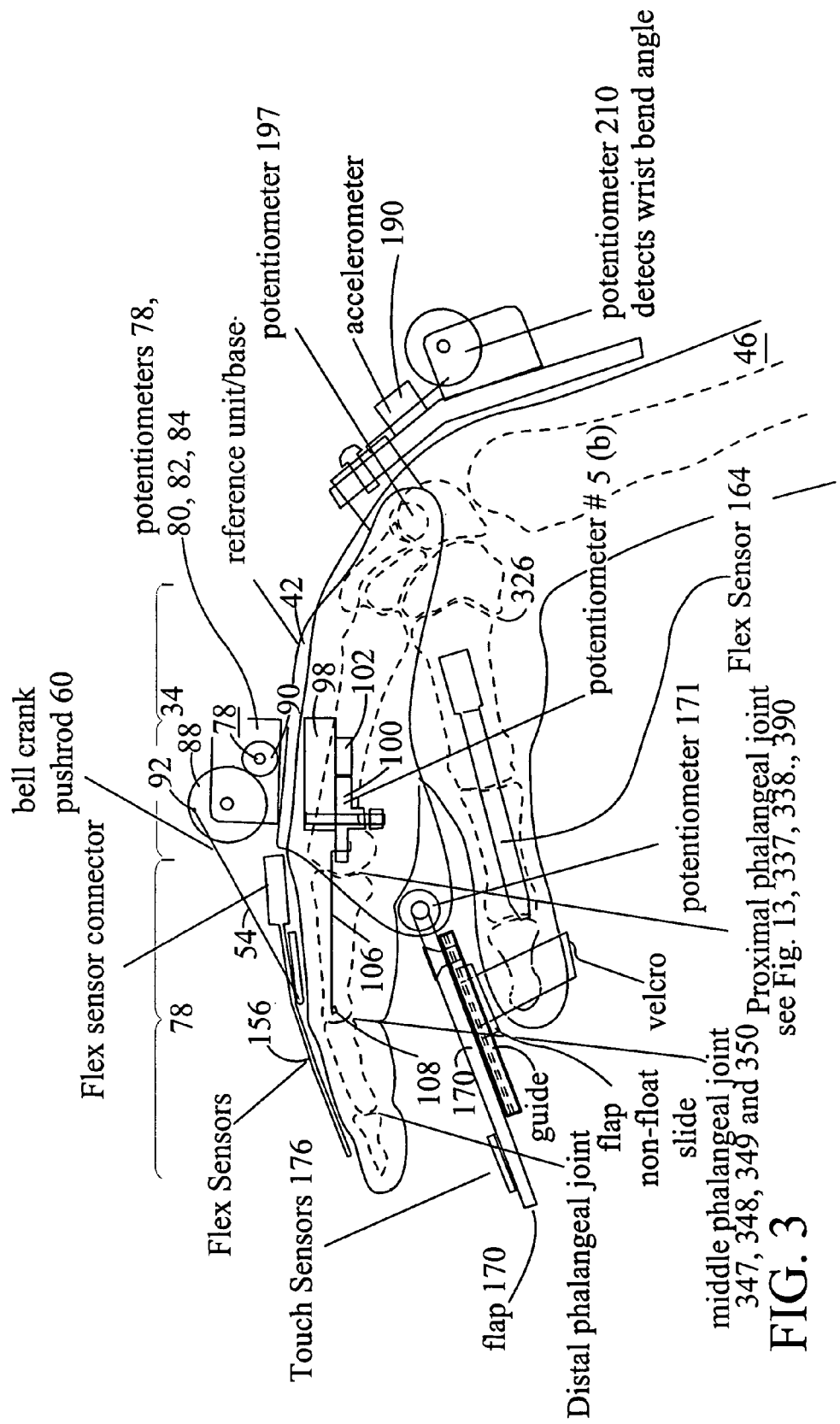
FIG. 3 is a profile view of the sensor glove illustrating the bending of the index finger to stimulate the potentiometer and flex sensor.
Figure 4:
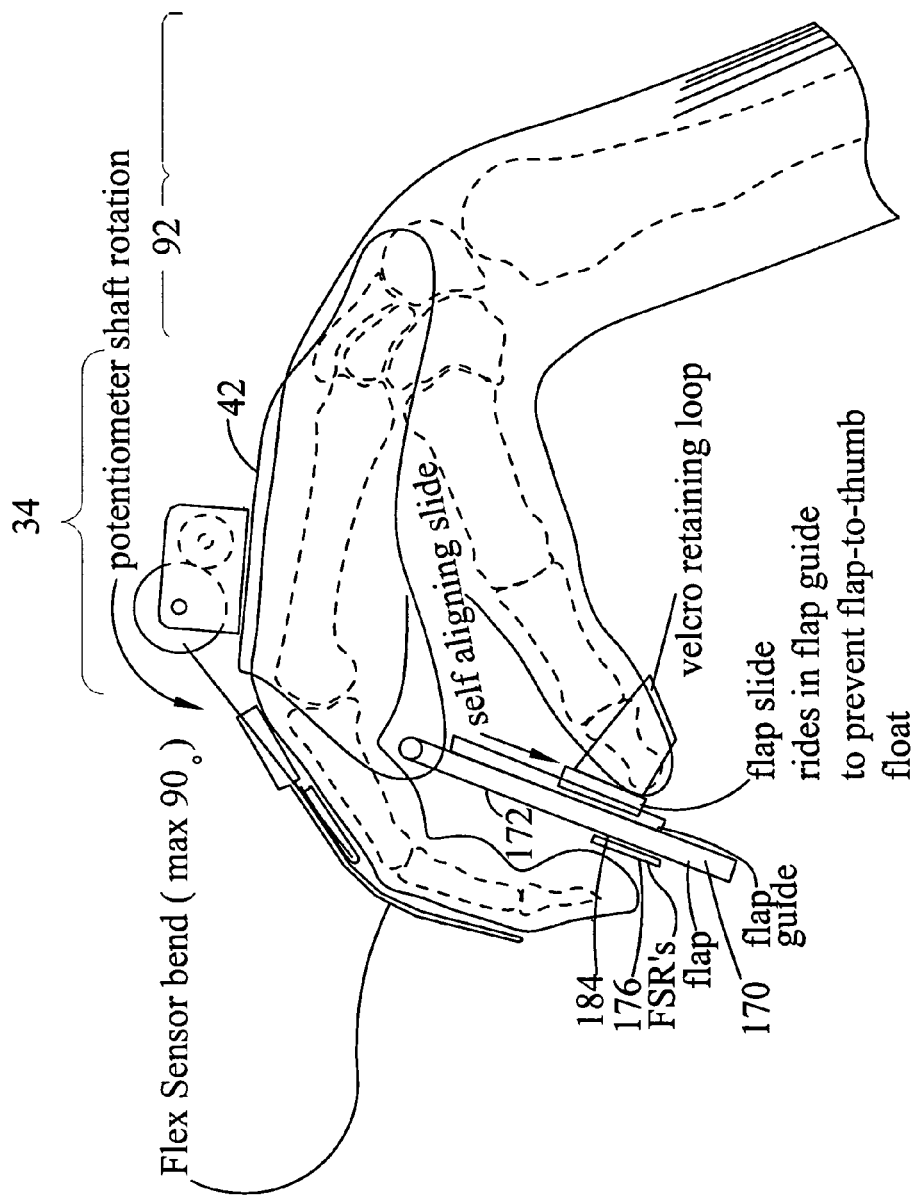
FIG. 4 is a profile view of the sensor glove illustrating the bending of the index finger to stimulate the FSR (force sensitive resistor) supported by the flap, the flap being supported by the thumb from below.
Figure 13:
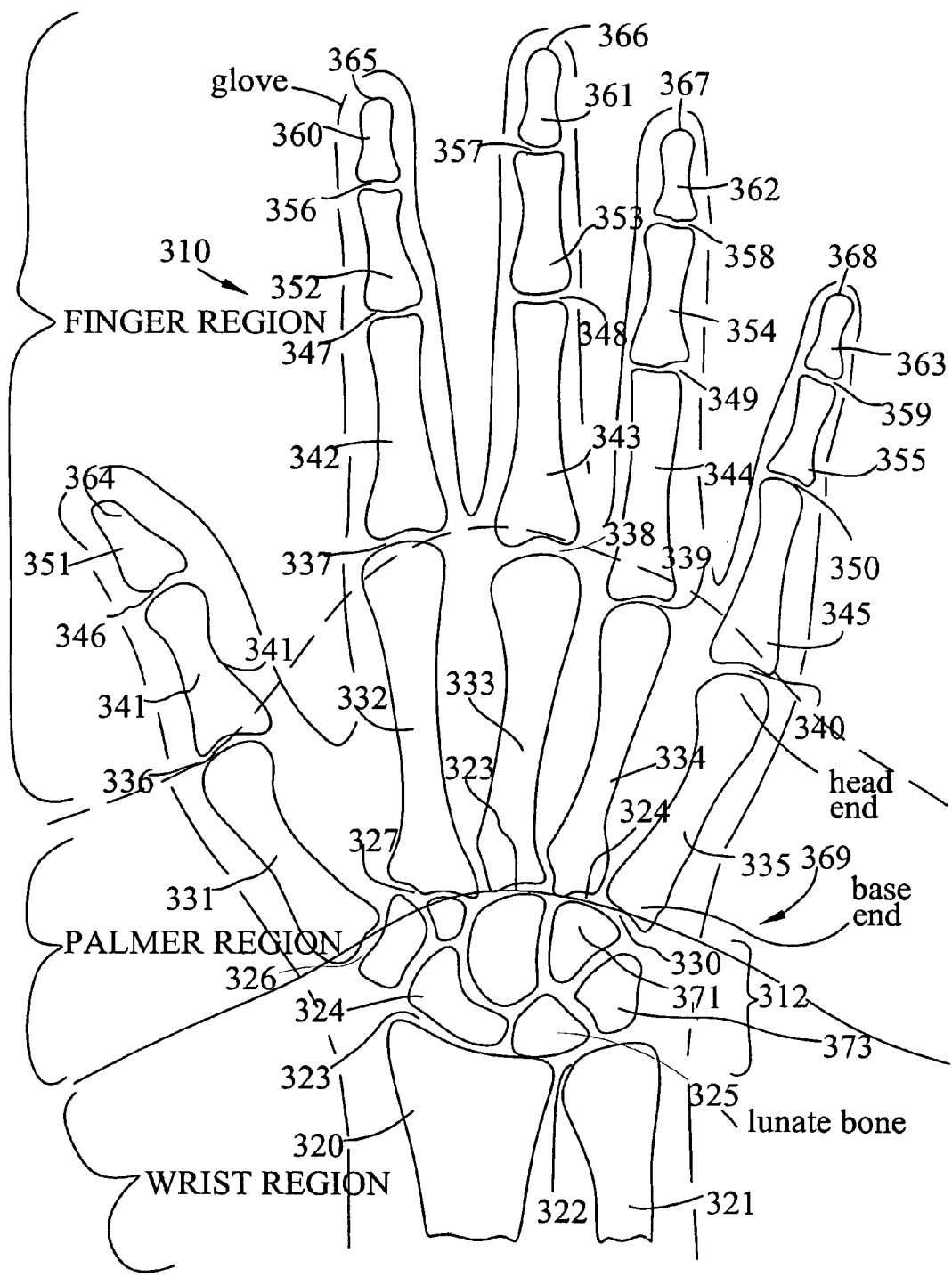
FIG. 13 is a schematic anatomical view of the right human hand showing the dorsal-side detail, an outline of the sensor glove with its respective regions being shown in phantom.

Bracket 28 shows the limits of a finger region which locates the glove fingers or the fingers of the glove. With reference to FIGS. 3, 4 and 13, the finger region extends from the metacarpalphalangeal joint 337, 338, 339 and 340 to the finger tip.

On FIG. 13, phantom line 32 passes through the metacarpalphalangeal joint 337, 338, 339 and 340 to characterize the location of the proximal end of the finger region, i.e. the location of the end of the finger sleeves away from the tips of the fingers.

Bracket 34 shows the limits of the palmer region. With reference to FIG. 13, the palmer region resides between phantom lines 32 and 36.

Bracket 34 shows the limits of a wrist region which extends to include a portion of the radius bone 320 and the ulna bone 321. The distal portion of the wrist region extends from the radiocarple joint 323, 324, 330 at the base end of the metacarpal bone 333 and the passage of phantom line 36 to the distal end of the radius bone 320 and the ulna bone 321 and the passage of phantom line 38.

In the sensor glove, at lease one finger region has a finger sleeve, such as the sleeve 40 that covers the index finger 365 is worn on a finger. However, in the more practical arrangements such as that of FIG. 1 and subsequent figures, all four fingers are inserted into respective finger sleeves that resides within the finger region of bracket 28.

Referring now to FIGS. 1-9, a rigid reference base 42 is shown in various positions. The rigid reference base has a longitudinal axis represented by phantom line 44 that extends in a direction from the forearm 46 to the finger region of bracket 28. A top surface 50 and an underside 52 are shown in FIG. 3. The rigid reference base underside 52 is coupled to the dorsal surface of the palmer region of the glove. The glove it typically made of a durable and playable fabric. As the performer inserts a hand into the glove and the fingers enter the finger region of the glove, the glove positions the rigid reference base to the position shown above the palma region 34 as shown in FIGS. 3-5.

Vertical Finger Motion to Pot Control Input

Pushrods 54, 56, 58 and 60 shown on FIGS. 1-5 represent a mechanical link and a means for coupling motion between the dorsal or top surface of the finger region at a respective point of connection such as at 62, 64, 66, 68 and the rigid reference base to a control input for a pot as at respective points of connection 70, 72, 74 and 76 to change the resistance of a respective pot 78, 80, 82, 84 in response to a bending motion of the respective finger in the finger region 28 with respect to the rigid reference base 42.

Index Finger Vertical and Horizontal Motion to a Control Input

Each of the pots 78, 80, 82, 84 are vertical motion sensing pots in that they tend to sense the vertical motion of a respective finger. Each respective pot has a case coupled to the top of the rigid reference base 42 and an input axis or control shaft that is positioned transverse to the longitudinal axis 44 of the hand and the rigid reference base 42. The input axis of each vertical sensing pot that is shown is above the top surface of the rigid reference base 42.

Pot Control Input Rotation Gain with Gearing

FIG. 3 shows a first gear 88 rotating in a vertical plane above the rigid reference base 42 with a rotational axis transverse to the longitudinal axis 44 of the rigid reference base. The first gear is meshed with and drives a smaller gear 90 that rotates the control input shaft of pot 78. It can be seen that a small rotation of the larger gear 88 will translate into a larger angle of rotation of the control shaft and the gain will be a function of the diameters of the two gears 88 and 90. In this arrangement, a small motion of the finger in the up or down direction, can put the push rod 54 into compression or tension and thereby produce a corresponding linear and tangential motion at the crank hole 92 on the periphery of gear 88. A small rotation of gear 88 can be scheduled or designed to produce a larger angular rotation of the smaller gear 90. The result is a gain in angular rotation that is a function of the ratio of the diameters of gear 88 and gear 90.

In the embodiment of FIG. 3 and subsequent, the vertical sensing pots each have an input axis that has a shaft with a gear affixed to the control input shaft to the pot. In an embodiment where angular gain is needed, the second gear such as 90 is then mounted co-planar with the first such as 88. The first gear, such as gear 90, serves as a bell crank and the ratio of the diameters of the two gears controls the angular gain. In an alternative embodiment, rotational resistors or pots are used that have a smaller required range of rotation for a complete travel of the internal wiper thereby reducing the need for a second gear. In such arrangements, a single gear is used on the shaft of the pot and the crank hole such as 92 is drilled in the gear driving the shaft of the pot.

The gears used on the test unit were plastic off the shelf parts. FIG. 12*a* through 12*c* are schematic drawings that show the features of gears that were used. Gears may be formed from alternative materials depending on the application and condition of use as well as cost. The set-up typically requires that the crank hole on the first or bell crank gear be positioned with the finger positioned and the control set to a mid-range or quiescent value. The hole is positioned to be as close to tangential to the push rod link as practical.

Index Finger Vertical and Horizontal Position Control

FIG. 2 and FIG. 3 shows index finger horizontal sensing pot 98 that uses a first or bell crank gear 100 to drive a control shaft input gear 102, both gears being mounted to be in a horizontal plane. Side-to-side motion of the index finger drives the rim of the first gear 100 thereby providing rotation to the control shaft input gear 102 with an angular gain controlled by the ratio of the diameter of the first gear 100 divided by the diameter of the second gear 102.

In the embodiment of FIG. 2 and FIG. 3, the horizontal motion sensing pot 98 has a case coupled to a vertical flange integrally coupled to the top of or to the side of (a flange side) the rigid reference base 42. The horizontal motion sensing pot has an input axis normal to the plane of the palmer region. The input axis of the horizontal sensing pot 98 has a shaft with a bell crank thereon. FIG. 3 shows link 106 coupling the distal surface of the finger region of the index finger at mooring point 108 with an arm of the horizontal sensing pot bell crank gear 100 to provide rotational motion of the horizontal gear in a horizontal plane. The bell crank gear 100 is positively linked to the control shaft gear 102 which drives the input axis shaft of the pot 98 in response to a horizontal motion of the top surface of the index finger region at mooring point 108.

Independent Thumb Motion Sensing in Two Degrees

Figure 9:
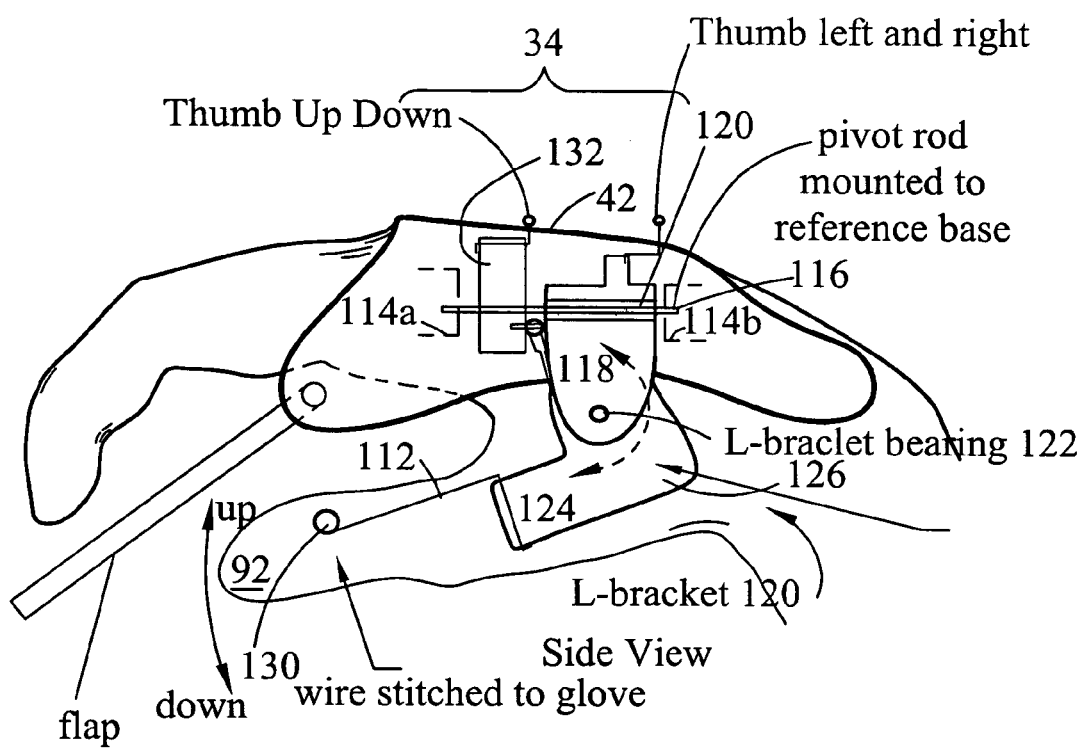
FIG. 9 is a side view of a mechanical means for translating a first and second degree of freedom of motion of the thumb with respect to the rigid reference base into a thumb control signal.
Figure 10:
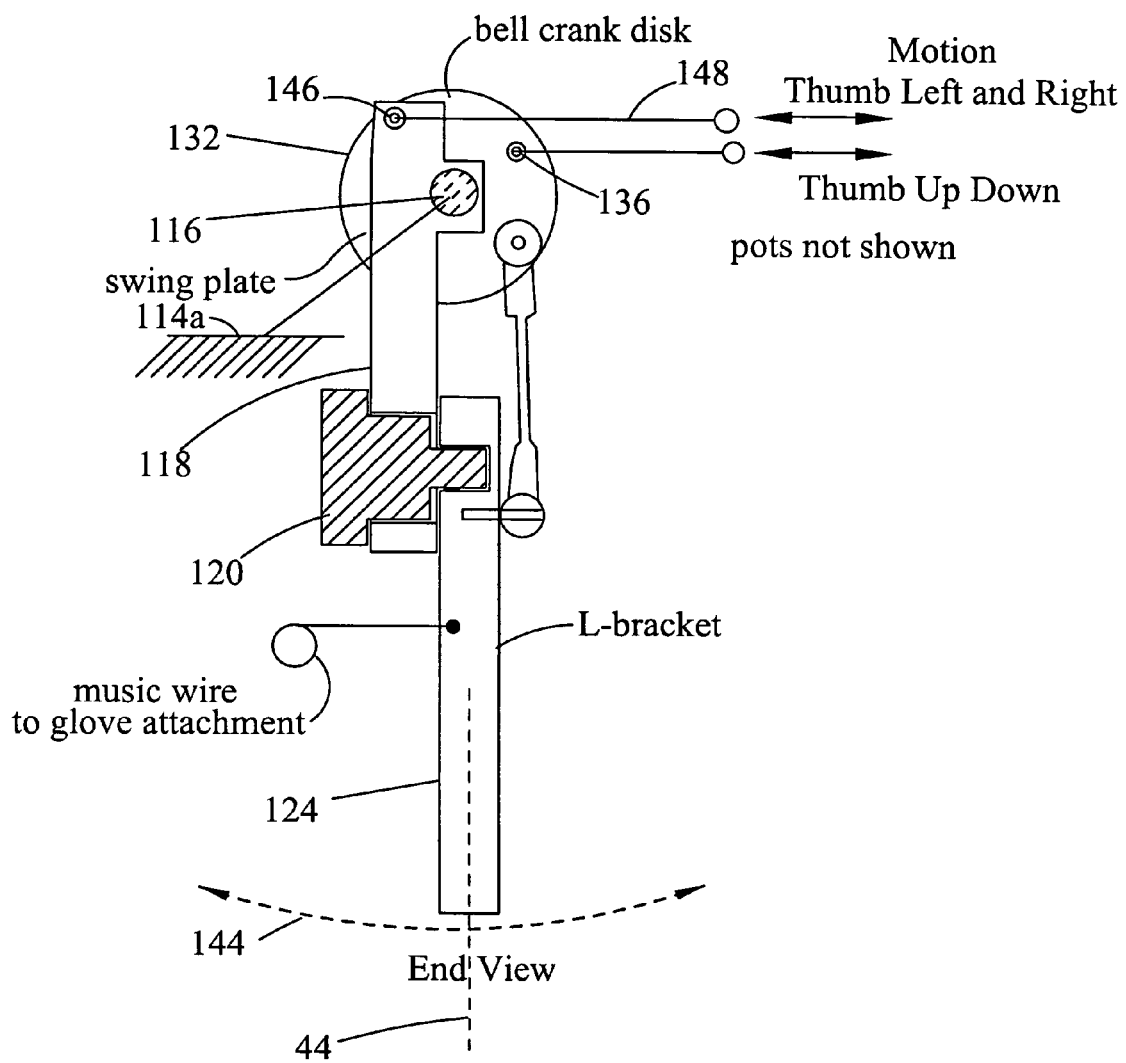
FIG. 10 is an end view of a mechanical means for translating a first and second degree of freedom of motion of the thumb with respect to the rigid reference base into a thumb control signal.
Figure 11:
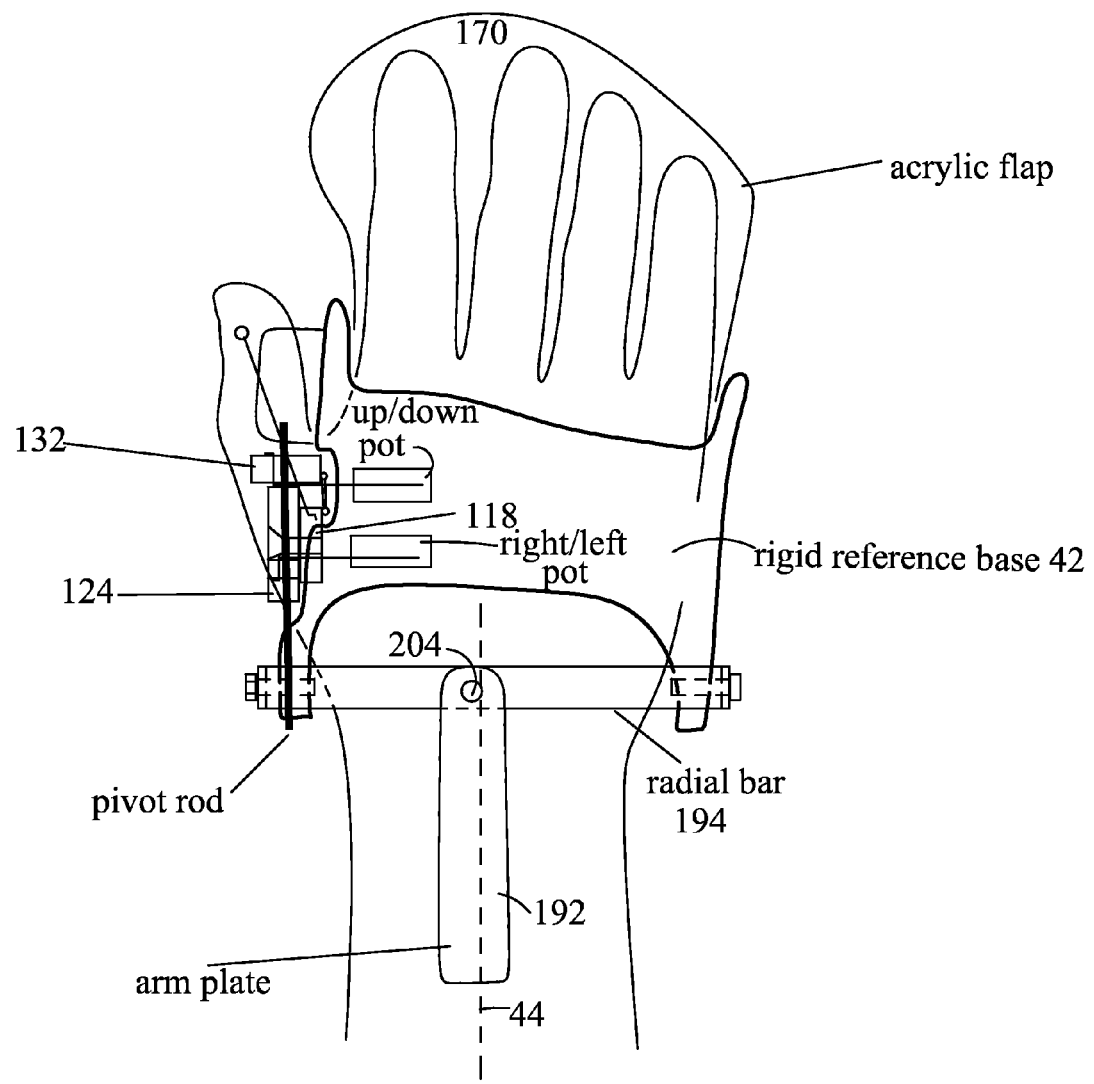
FIG. 11 is a plan view of a mechanical means for translating a first and second degree of freedom of motion of the thumb with respect to the rigid reference base into a thumb control signal.

FIGS. 9-11 show an embodiment of a means represented by the assembly under brackets 110 driven by a single a mechanical link 112 for translating a first degree of freedom, such as up and down, or pitch, and a and second degree of freedom of motion, such as left and right or yaw, of the thumb with respect to the rigid reference base 42 into a thumb control signal from each of two separate pots (not shown). The control signal from each of the pots results from the independent linear or rotational motion of the control of each respective pot.

FIGS. 9-11 provide an assembly for independently sensing vertical motion of the thumb, in a thumb finger region, with respect to the top surface of the rigid reference base and for independently sensing horizontal motion of the thumb with respect to the top surface of the rigid reference base. and for providing a vertical thumb motion signal and a horizontal thumb motion signal to a signal conditioner.

Referring to FIG. 9, brackets 114*a* and 114*b* shown in phantom represent a frame for mounting holding a bearing rod 116 in horizontal relation with the top surface of the rigid reference base 42. The bearing rod 116 is positioned in substantially co-parallel relation and displaced to be on the thumb side of the top surface of the rigid reference base 42. Swing plate 118 has a displaced bore 120 for receiving the bearing rod.

The swing plate 118 is free to rotate on the bearing rod 116 in a plane transverse to the longitudinal axis of the rigid reference base 42. The swing plate 118 has a swing plate bearing 122 with an axis normal to the plane of the swing plate. An L-bracket 124 is coupled to the swing plate 118 by the swing plate bearing 120 positioned in an upper region 126 of the L-bracket. The lower region of the L-bracket is formed to extend in the direction that the thumb extends in. The L-bracket is free to rotate on the swing plate bearing 120 in the plane of the swing plate. The lower region of the L-bracket has a distal end 124 positioned along the length of the thumb. The L-bracket has a proximal end 126 under the swing plate bearing 120.

The single mechanical link or wire 112 flexibly couples the distal end of the L-bracket to the thumb finger region at anchor point 130. The wire 112 transfers the motion of the thumb in the vertical plane and in the horizontal plane to the distal end of the L-bracket 124.

A disk shaped thumb motion bell crank 132 is supported and free to pivot on the bearing rod 116. The disk shaped thumb motion bell crank 132 has a vertical pivot bore 134 and a horizontal transfer bore 136.

Ball linkage rod 138 has a ball linkage on a lower end 140 coupled to the L=bracket and a ball linkage on an upper end 142 coupled to the vertical pivot bore 134 in the thumb motion bell crank. Lateral motion of the mechanical link or wire 112 as in the yaw of the thumb translates into a side to side motion of the L-bracket as suggested by phantom arc 144 in FIG. 10.

The side to side or yaw motion of the thumb results in a right to left motion at the top of the swing plate 118 and a corresponding right to left motion of the crank hole 146 which transfers right to left motion through left right rod 148 to a right to left signal generating pot not shown in the Figures. Concurrently and independently, an up and down motion of the link or wire 112 rocks the distal end 124 of the L-bracket rotating it on swing plate bearing 122.

If the thumb moves down, the L-bracket rotates counter clockwise. With the ball linkage on a lower end 140 coupled to a point to the right of swing plate bearing 122 as shown on FIG. 9, the proposed motion translates into a rise in the ball link rod 138 with a corresponding rise in the pivot bore 134 resulting in a counter clockwise rotation of the bell crank disk 132. A counter clockwise rotation of the bell crank disk results in a left to right translation of the horizontal transfer bore 136 putting the up down rod 152 into tension. The motions of the two rods are therefore independent of each other as required by operation of the assembly.

Figure 5:
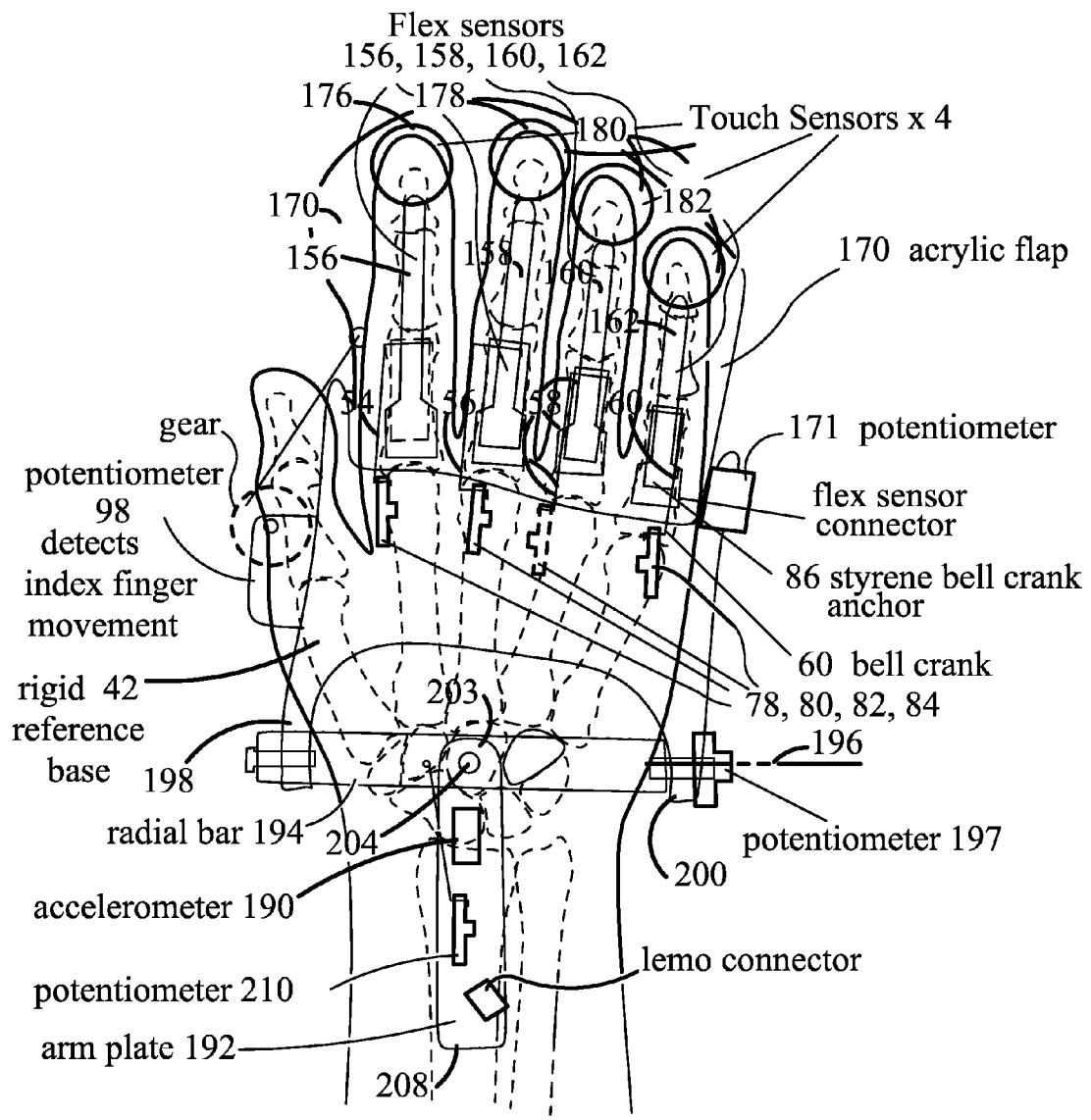
FIG. 5 is a plan view of the sensor glove of FIG. 1 from the dorsal or back side of the hand showing the location of four force sensor resistors shown as circles.
Figure 6:
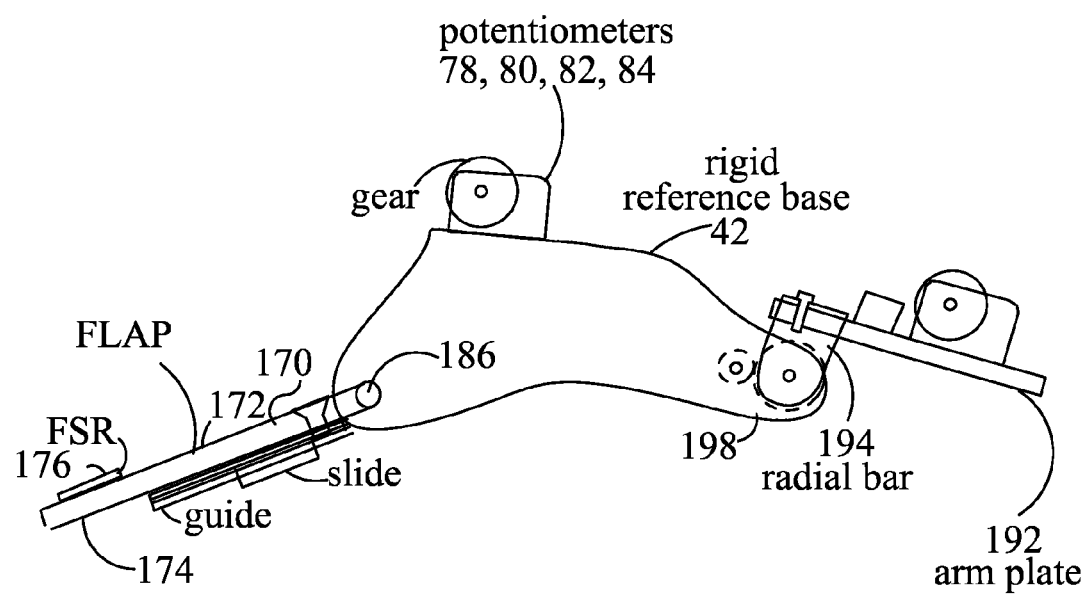
FIG. 6 is a schematic side view of an assembly showing a flap, rigid reference base left flange and the left edge of the arm plate.

FIG. 3 and FIG. 4 show bend sensor 156 in a side view, the sensor being bent in FIG. 4 by closure of the hand. In each case, the bend sensor is coupled to the index finger. The bend sensor is mechanically coupled to the dorsal or top side of a gloved finger in the finger region. Each of the bend sensors shown in FIGS. 1 and 2 and more particularly bend sensors 156, 158, 160 and 162 shown in FIG. 5 are positioned to be in close proximity to a sense location for providing a fine bend signal characterizing a bend motion of the gloved finger region corresponding to the sense location.

Flap, and Flap Angle Sensing

FIG. 3, 4 and FIG. 46 show a rigid flap 170 in a side profile. The flap 170 is shown in a plan view in FIGS. 5 and 7. The flap 170 is formed from a rigid material such as fiberglass or plastic. The flap has an upper surface shown in FIG. 6 as 172 and a lower surface 174. Referring to FIG. 5, force sensitive resistors (FSR) 176, 178, 180, 182 are shown on the top surface of flap 170. The force sensitive resistors are shown coupled to the rigid flap upper surface 172.

Referring again to FIGS. 6 and 7, the rigid flap 170 is pivotally coupled to the rigid reference base 42 on rotational axis 186 that is shown transverse to the extended direction of a finger. As shown in FIG. 4, the force sensitive resistor, such as FSR 176, is positioned on the rigid flap upper surface 172 at a location 184 under the finger. The rigid flap lower side 174 is supported or raised by motion of the ball of the thumb to permit the ball of the finger to provide a force to the force sensitive resistor to change the resistance of the force sensitive resistor in response to an increase in pressure between the thumb and the finger with the rigid flap and force sensitive resistor therebetween.

Figure 7:
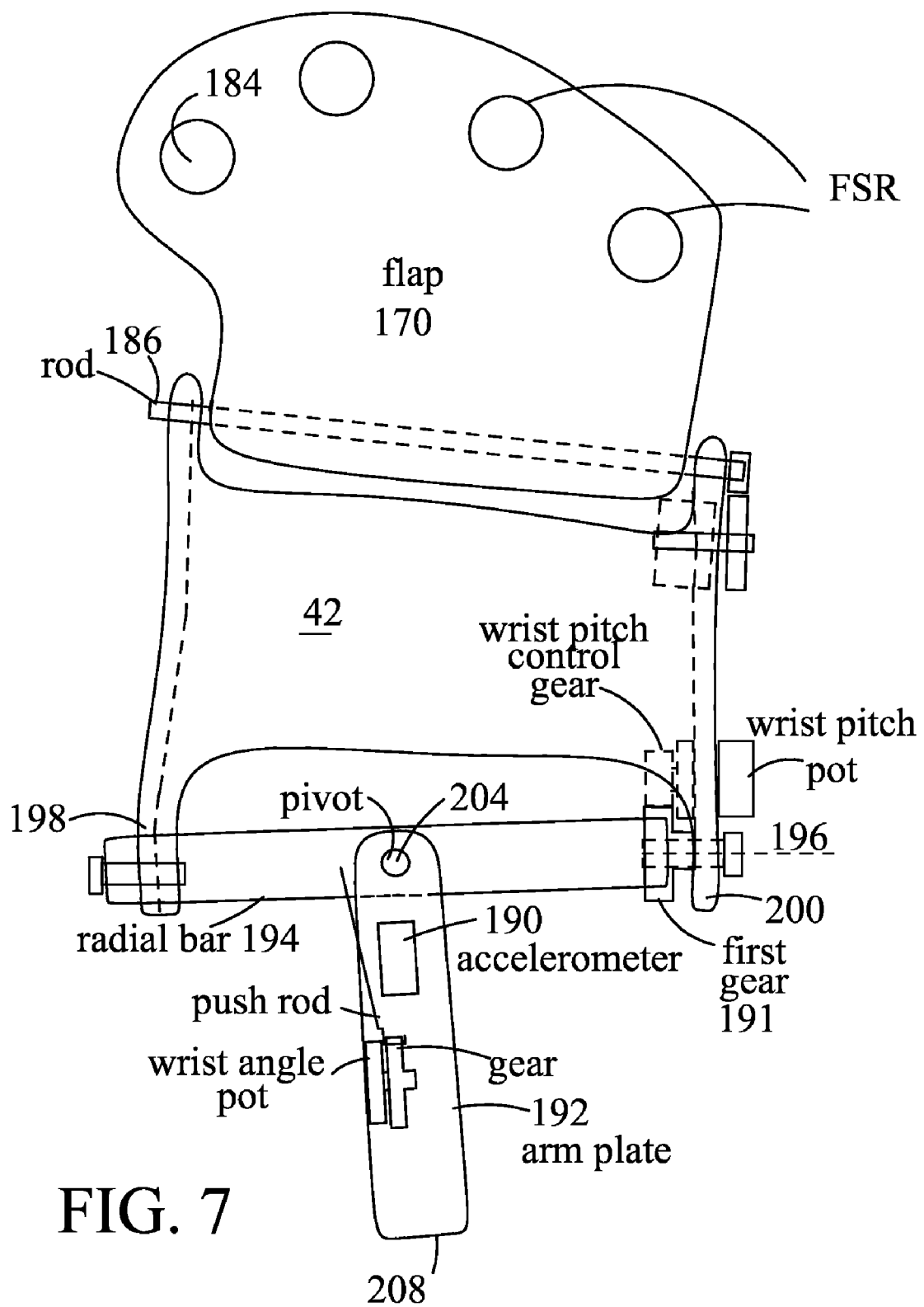
FIG. 7 is a schematic plan view of the assembly of FIG. 6 showing the flap, rigid reference base left and right flanges in phantom the arm plate.

FIG. 7 shows flap pot 171 coupled to the right flange 198 of the rigid reference base 42. A first gear 173 is coupled to the rotational axis 186 of the flap 170. As the flap rotates on axis 186, first gear 173 drives a second gear 175 that is coupled to the shaft input for the flap position pot 171. Use of a first and second gear makes it possible to scale the angle rate of the flap shaft to the angle rate of the control shaft for the flap pot 171.

Accelerometer on Arm Plate.

FIG. 7 shows the addition of an accelerometer 190 onto arm plate 192 which is pivotally coupled to radial bar 194. The rigid reference base 42 has a longitudinal axis 44 discussed earlier that extends from the forearm or wrist region to the palmer region. The wrist region, the wrist region extends toward the forearm past the base ends of the metacarpal bones rearward beyond and covers the scaphoid and lunate bones.

The rigid reference base 42 has a top surface and an underside that is coupled to the dorsal surface of the palmer region or to the top of the palmer side of the glove. The rigid reference base covers the palmer region and has integral right and left flanges that extend downward below the dorsal surface of the palmer region. The right and left flanges cover the hand, and extend their cover rearward to a proximal end terminating after the wrist region.

FIG. 5 shows the radial bar 194 pivotally coupled to a first pivot axis 196 that is transverse to and that passes through the proximal end of the right and left flanges 198, 200 of the rigid reference base 42. FIGS. 5 and 7 show the arm plate 192 having a longitudinal axis that extends from a distal or far end 202 and that is pivotally coupled at pivot 204 to the radial bar 192 and a proximal end 208 attached to the dorsal side of the glove. The attachment is under the view of FIG. 6 and FIG. 7.

The accelerometer 190 has at least a first sensitive axis, In practice, an accelerometer having two or three axes is used. The accelerometer 190 is coupled to the bracket plate to provide at least a first acceleration signal corresponding to acceleration experienced along its first sensitive axis. In the example of FIGS. 5 and 7, the sensitive axis of the accelerometer 190 is fixed to the longitudinal axis 44 of the arm plate 192 and the forearm. The sensitive axis of the accelerometer 190 substantially decoupled from rotation of the hand with respect to the forearm by operation of the pivot coupling at the distal end of the arm plate.

Gear Drive for Radial Bar Pitch Rotation Pot

FIG. 7 shows a first gear 191 on the inside of the radial bar right flange. The first gear 191 rotates with the radial bar around the rotation axis 196. The first gear 191 is larger than a control shaft gear 193 on the control shaft of the wrist pitch pot 197. As the radial bar 194 rotates on its axis 196, it rotates the first gear 191. As the first gear rotates, it drives the control shaft gear 193 on the control shaft of pitch pot 197 thereby causing the pitch pot 197 to produce a signal characterizing the angular position of the radial arm 194 with respect to the rigid reference base 42.

FIGS. 1, 2 and 3 illustrate and provide an overview of sensor glove, the position of the hand in the sensor glove, the bones within the hand and key mechanical features of the glove that include components such as potentiometers, flex sensors, accelerometers, force sensing resistors (FSR, touch sensors), and the exoskeletal structures they interact with.

FIGS. 1-12 show that the Sensor glove is assembled from: a flexible fabric glove base; a rigid plastic reference unit/base; a series of potentiometers and sensors; and circuitry and wiring. The fabric glove is predominantly made from a two-way stretch satin Lycra fabric, the stretch allowing width expansion only, assuring close fitting over a wide range of hand sizes. Along each of the dorsal aspect of the fingers, from the proximal to the middle phalangeal joints, a thin rectangular pocket or sleeve, from a four-way stretch polyester lycra, is sewn open ended to the satin lycra fabric, creating a housing for the flex sensor and styrene bell crank anchor. The palmar aspect of the glove has a four-way stretch lycra fabric milled with ¼" inch holes for ventilation. Webbing material is sewn to the wrist and mid arm sections, to anchor the glove to the wearer. Velcro fasteners complete the webbing adjustments.

FIGS. 1, 2 and 3 show the plastic rigid reference base 42 as a rigid exoskeleton of the hand. The rigid reference base 42 sits exclusively along the metacarpal region. Its purpose is to act as a reference body or frame on which all of the digit potentiometers 78,80,82,84,98,171 are mounted. It mirrors the arc and shape of the metacarpal region, creating an ergonomic form that sits comfortably on top of the hand. Side flanges extend at 90° to the dorsal metacarpal region, in order to support the acrylic flap 170 and associated potentiometer 171, proprietary circuitry and an additional side mounted potentiometer 98. The side flanges also extend towards the carpal and have two pivot axes, which intersect the center of the carpal region and act as a positional reference of the wrist, and to house the potentiometer 197 that measures the up and down movement of the wrist.

The two pivot axes are the mooring points for a radial bar 194 that connects from the ulna side to the radius side, and in turn is the mooring point for the arm plate 192, which pivots centrally from the radial bar, and is sewn to the arm section of the flexible fabric glove base.

A total of seven 5k potentiometers are mounted upon the plastic rigid reference base 42. One 5k potentiometer is mounted to the arm plate 192. Totaling 8 potentiometers. Two types of potentiometers have been used. The types used included: (i) Clarostat 5k: part #590SX1N56S502SP, (ii) Honeywell-Nei 5k sensorcube: MC series part #MC6CE1A502X003.

As shown in FIG. 1 and more particularly in FIGS. 3 and 4, the four potentiometers 78, 80, 82 and 84 have their axis above the proximal phalangeal joints of the four digits (a). FIG. 13 discussed later, will provide a more detailed explanation of the bones in a right human hand.

Attached to each potentiometer's input/output shaft is a ⅞ inch diameter nylon disk or gear. At the position of ⅛ inch from the outside edge of the nylon disk a 0.035 inch hole is drilled to accept a 0.032 inch music wire fabricated into the form of a bell crank 56. The other end of the bell crank is pivoting within a 0.035 drilled hole in the styrene bell crank anchor 86, located within the thin rectangular lycra pocket on the fabric glove base, and held in place with velcro on the underside of the styrene bell crank anchor with the matching velcro in the lycra pocket. The pivot for the styrene bell crank anchor is located at the middle phalangeal joint.

FIGS. 1 and 2 show Potentiometer 98 as side mounted, on the 90° side flange spanning the region of the index finger and thumb metacarpals, which captures the lateral movement or finger spread of the index finger (digitus secundus). The other end of the bell crank is fabricated into a small loop and sewn to the glove at the side of the middle phalangeal joint of the index finger (digitus secundus).

Potentiometer 171 is mounted on the side flange, by the pinky finger's (digitus quintus) proximal phalangeal joint, and receives motion from the acrylic flap 170, which is moved by the traversing of the thumb in an up and down motion. The acrylic rigid flap is attached to a stainless steel ⅛ inch shaft that is pivoted just below the line of the proximal phalangeal joints and runs parallel to said joints.

The acrylic flap 170 on FIG. 1 is not a representation of any part of a hand. The rigid flap is a nebulous hinge. It can be used in many ways. In the present embodiment it is used as a character's jaw, but it could be used as a thumb bend, etc. It is also the support/base for four FSR, (Force Sensing Resistor) 176,178,180, 182. Each FSR is lined up to meet the touch from each distal phalange.

Two options have been used: The first is an Interlink Electronics (Camarillo, Calif.): model #402 and model #405. Potentiometer #7 (d) is mounted at the wrist on the pivot axis from the ulnar side flange between the lower carpal and metacarpal joints, and measures the wrists up and down motion. Attached to the potentiometer's output shaft is a gear linkage, which is driven by the rotation of the radial bar 194.

Potentiometer 210 is mounted at the wrist above the lower radial and ulnar joint, and measures the wrist's side-to-side motion. Attached to the potentiometer's output shaft is a ⅞ inch diameter nylon disk or gear. At the position of ⅛ inch from the outside edge of the nylon disk a 0.035 inch hole is drilled to accept a 0.032 inch music wire fabricated into the form of a bell crank. The other end of the bell crank is pivoting around a 4-40 machine screw on the radial bar 194.

Flex Sensors

FIG. 2 shows five Flex sensors that are used in the glove. The components are designated as sensors 156, 158,160,162, 164. The Flex sensors used in the development of the invention Sensor Glove were from Flexpoint Sensor Systems (Draper, Utah) and the part numbers were #2000-1100.

The Flex sensors of FIG. 5 are comprised of carbon/polymer based ink coating on a flexible strip that changes resistance as it flexes. The Flex sensors can be bent at any point or combination of points along the 1½ inch long by ¼ inch wide by 0.015 thick strip with a combination of a single or multiple bends of up to a maximum of 90°. It's therefore self aligning, and will accept various phalangeal proportions without readjustment. It is placed within the thin rectangular pocket at each finger and thumb positions. The Flex Sensors measure the rotation of the finger's middle phalangeal joints, and the distal phalangeal joint rotation of the thumb.

Accelerometers.

FIGS. 1 and 2 show two or three axes accelerometers 190 placed on the arm plate 192 to capture the roll, pitch, yaw of the lower arm. Accelerometers used in the development included accelerometers from Analog Devices (Norwood, Mass.): and in particular, part #ADXL 311, 203, 322

Figure 8:
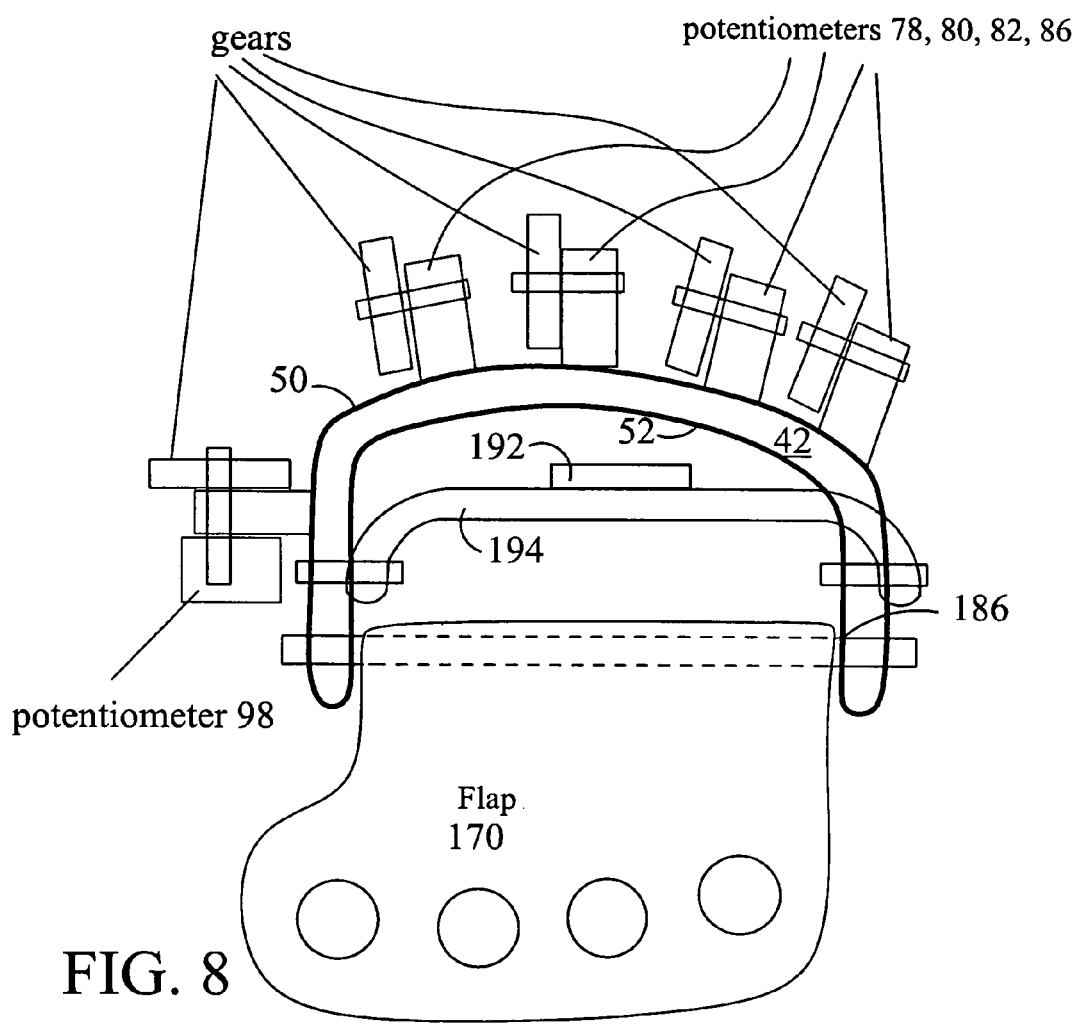
FIG. 8 is a schematic front, view of the assembly of FIG. 6 showing a flap, a forward edge view of the rigid reference base with the forward edge of the left and right flanges shown, the locations of five potentiometers and their respective control gears is shown.
Figure 14:
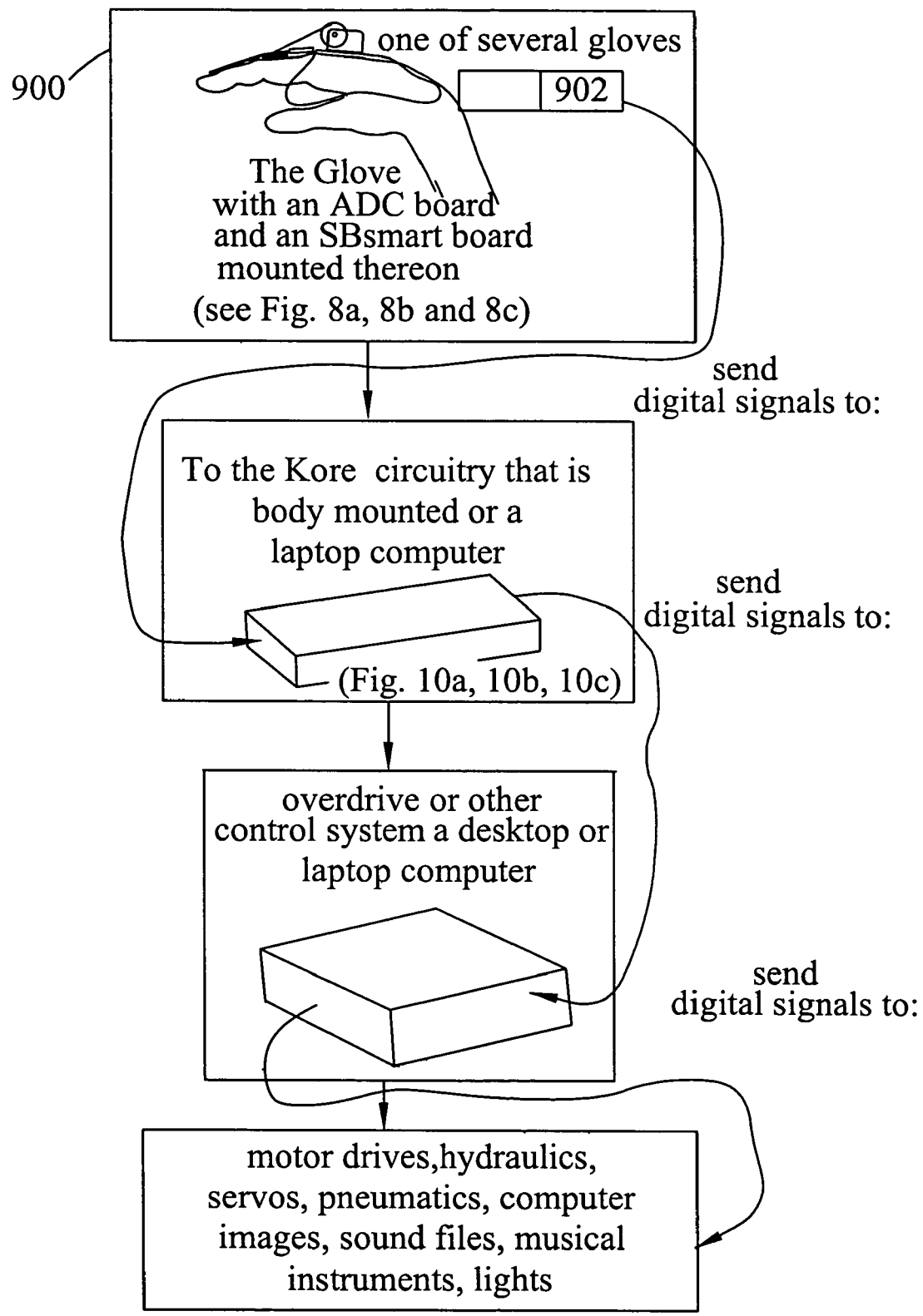
FIG. 14 is a flow chart expressing the overall relationship of the sensor glove and Kore circuitry as a system.

FIG. 14 is a an overview flow chart of the system. FIG. 1 shows a performers hand in the sensor glove. FIG. 2 also shows the performer's hand in the sensor glove but from a different view point. FIG. 7 is a block diagram of the SBsmart Circuit and a typical on-board sensor processing system. FIG. 8 is a block diagram of the On Glove Circuitry and the SBsmart ADC signal conditioning and sensors.

Figure 15:
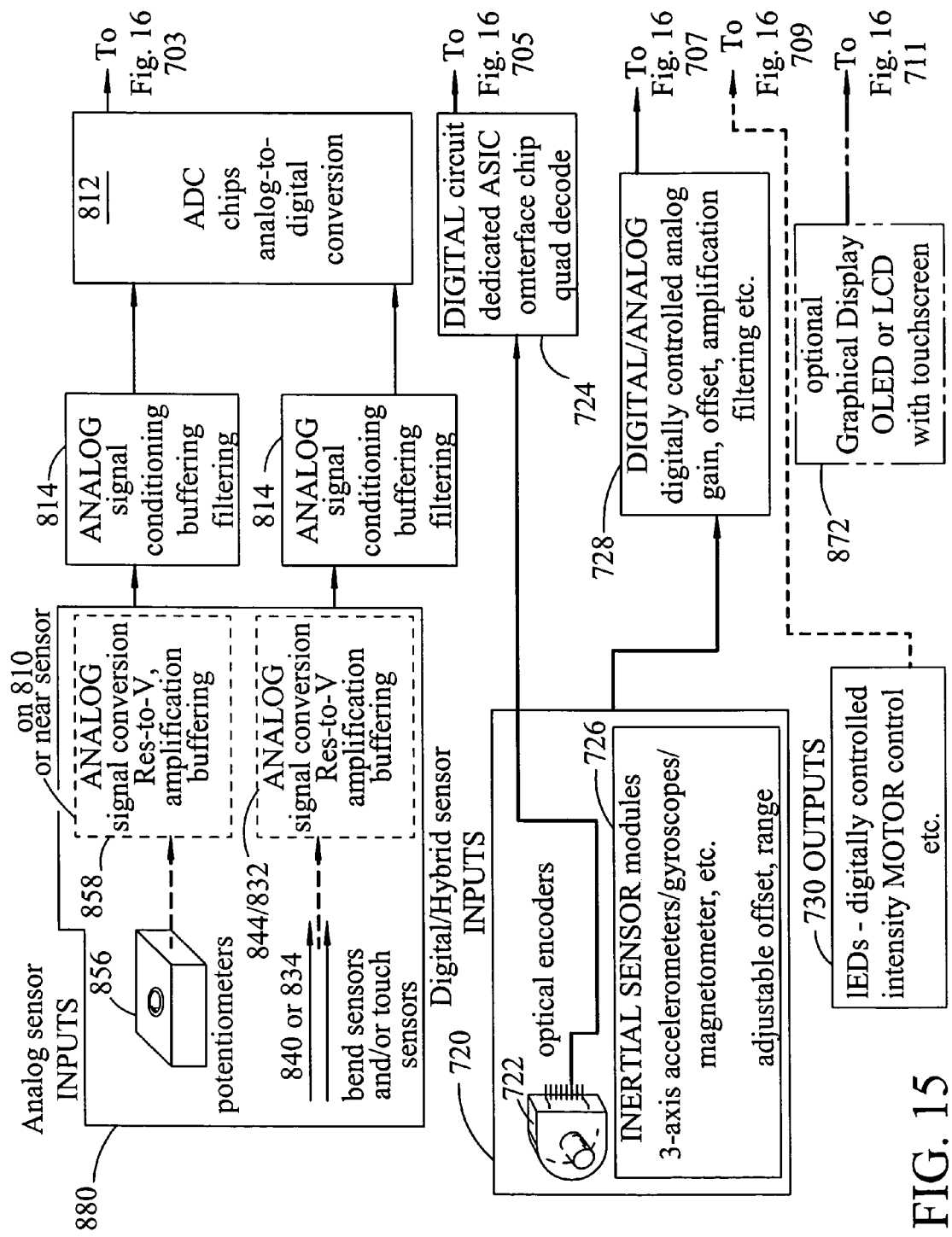
FIG. 15 is a flow chart showing types of analog inputs to the ADC board.
Figure 16:
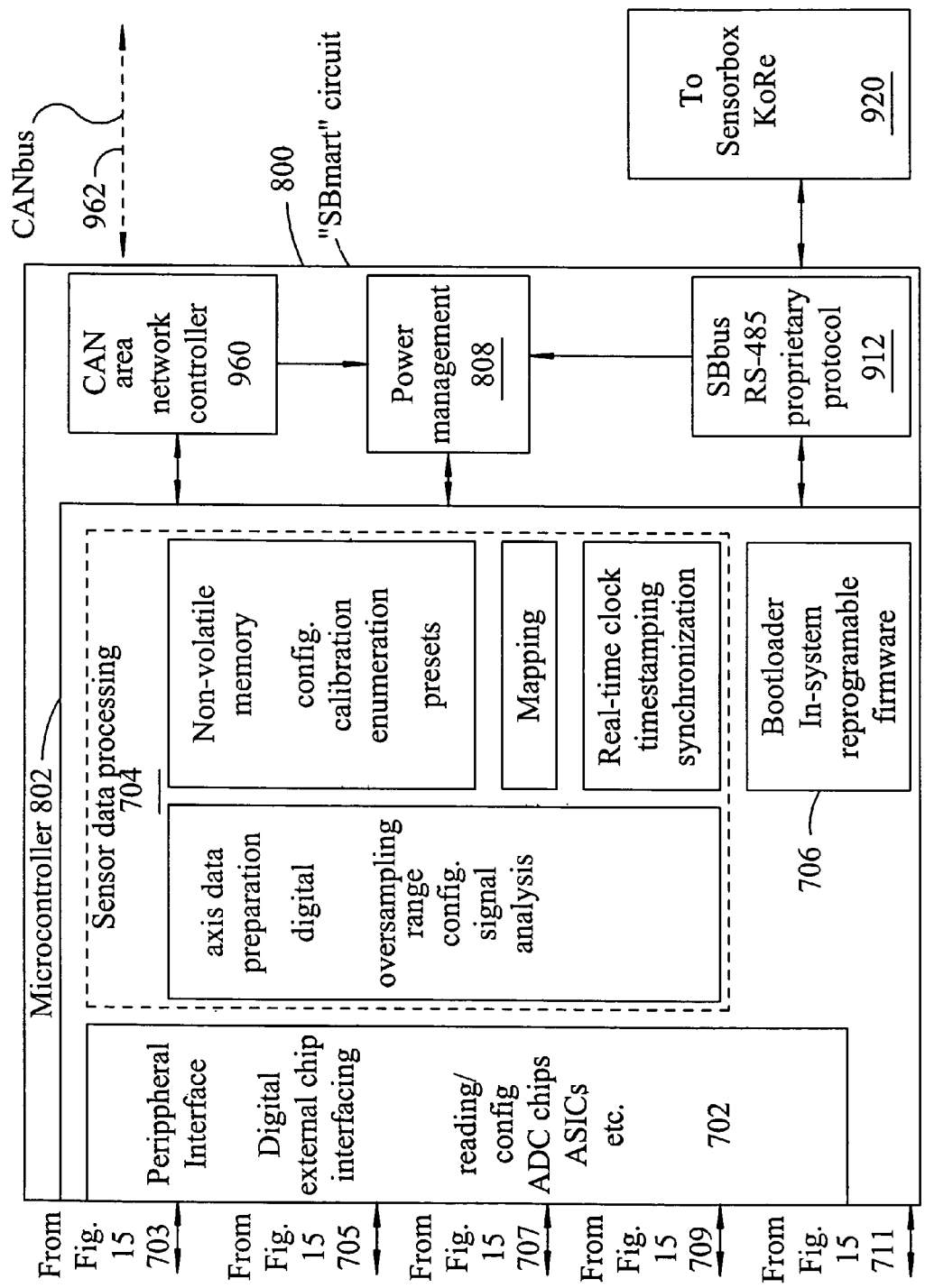
FIG. 16 is a flow chart showing inputs from FIG. 15 being processed by the SBsmart board on the sensor glove and output as digital signals to the KoRe module off the sensor glove.

The SBsmart Circuit:

FIGS. 15 and 16 shows how the SBsmart (800) circuit connects to various types of sensors and different inputs/outputs. Analog sensors (880) such as potentiometers (78, 856) and bend/touch sensors (156,840, 834) have their signals converted to a buffered and full-range voltage at the sensor and then connect to an analog-to-digital board (810) where any additional signal conditioning and filtering (814) is done before reaching the analog-to-digital chip (812).

The SBsmart circuit has a microprocessor (802) that can interface (702) to various types of ADC chips (812), DAC (digital-to-analog) chips, or other ASIC (application specific IC) (724, 728, 730) for connecting optical encoders (722), inertial sensor modules (726), various outputs (730) such as intensity controlled LEDs, motor controllers, etc., and optionally a graphical LCD or OLED display with or without touchscreen (872).

The on-board microcontroller (802) has sensor data processing (704) elements to allow for control over the sampling frequency, calibration, range of the inputs and outputs, as well as non-volatile memory to store/recall presets of these settings. A bootloader (706) provides a means for reprogramming the firmware of the microcontroller (802) remotely without any special hardware and without interrupting the operation of other SBsmarts on the SBbus.

By processing the sensor signals on-board the SBsmart, the signals can be dynamically pre-conditioned (through digitally controlled pre-ADC analog circuitry), accurately time-stamped (taking sensor latency into consideration and based on an internal real-time-clock and/or synchronized to an external clock master), tuned (filter/scaled/biased/oversampled), and sampled/analyzed at a very high speed, only outputting the final processed data as needed by the particular application.

Data and power are transmitted on the SBbus (914) via a RS-485 transceiver (912) and using a proprietary protocol for a high-speed half-duplex multidrop multimaster network. Alternately, an industry-standard CANbus (962) interface is provided via an on-board CAN controller and transceiver (960). Power management circuitry (808) assures overvoltage protection, monitoring of voltage/current, and low power modes.

Figure 17:
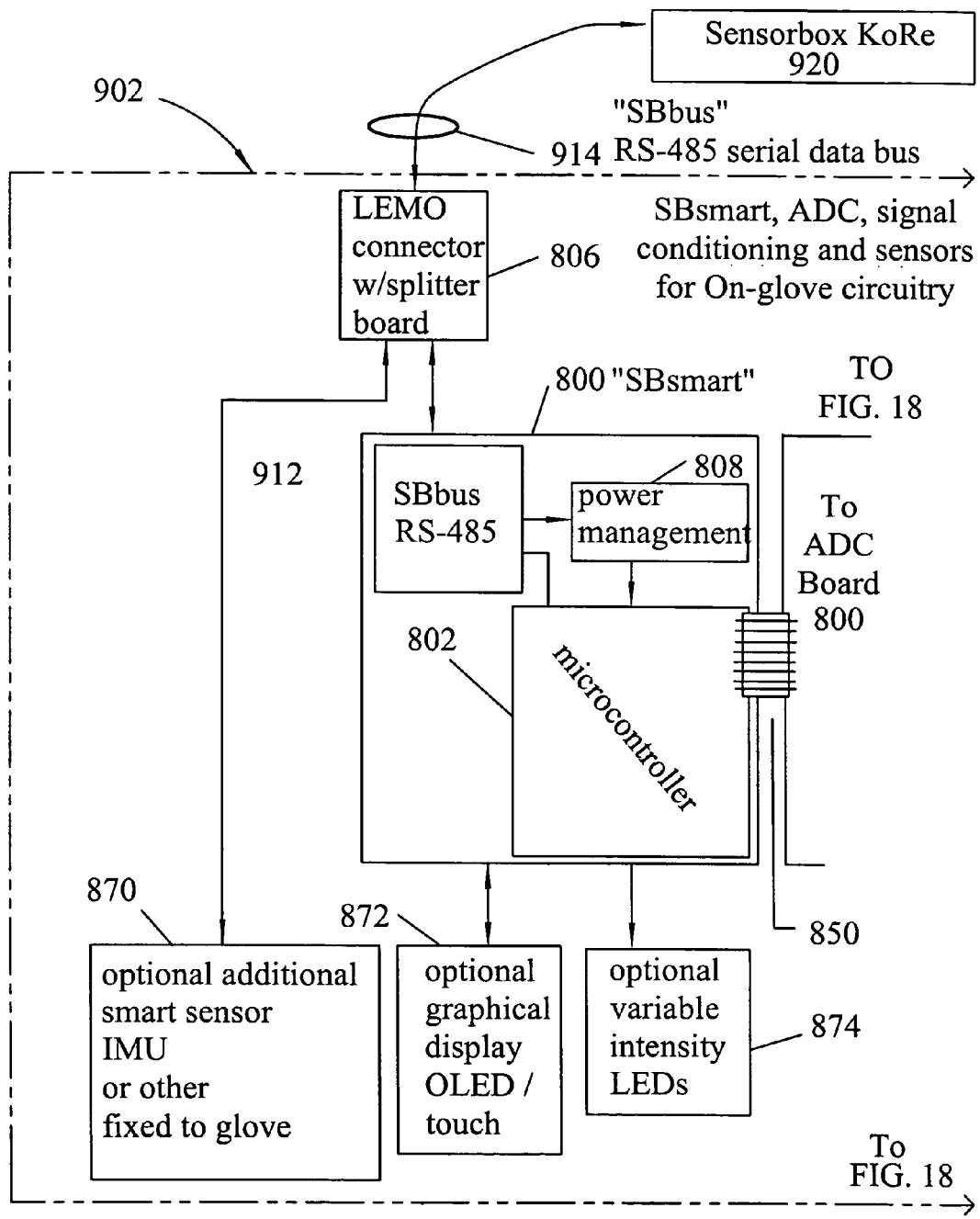
FIGS. 17, 18 and 19 are a linked block diagram showing the combined ADC board and the SBsmart board as blocks on the sensor glove.
Figure 18:
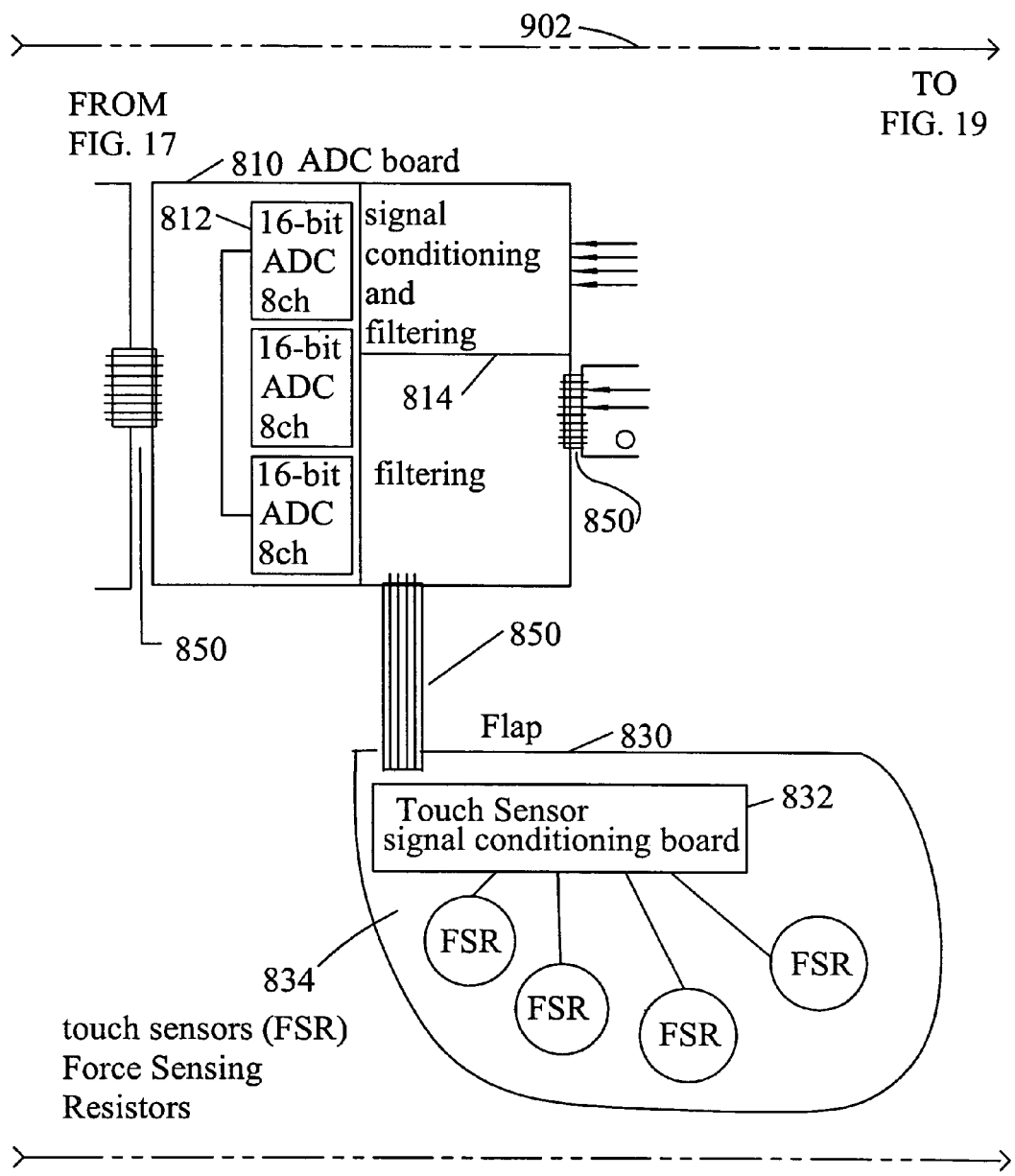
Figure 19:
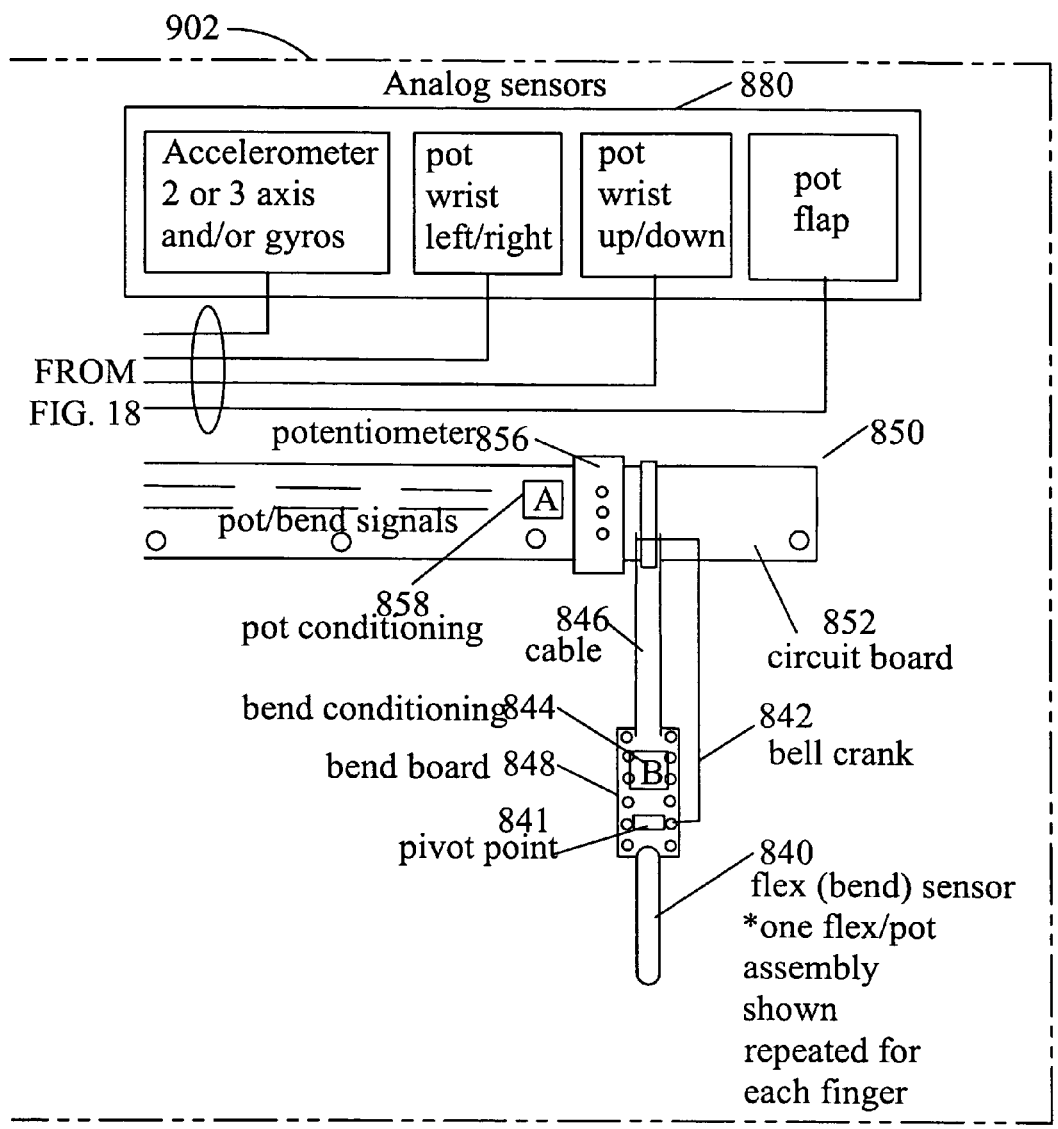
Figure 20:
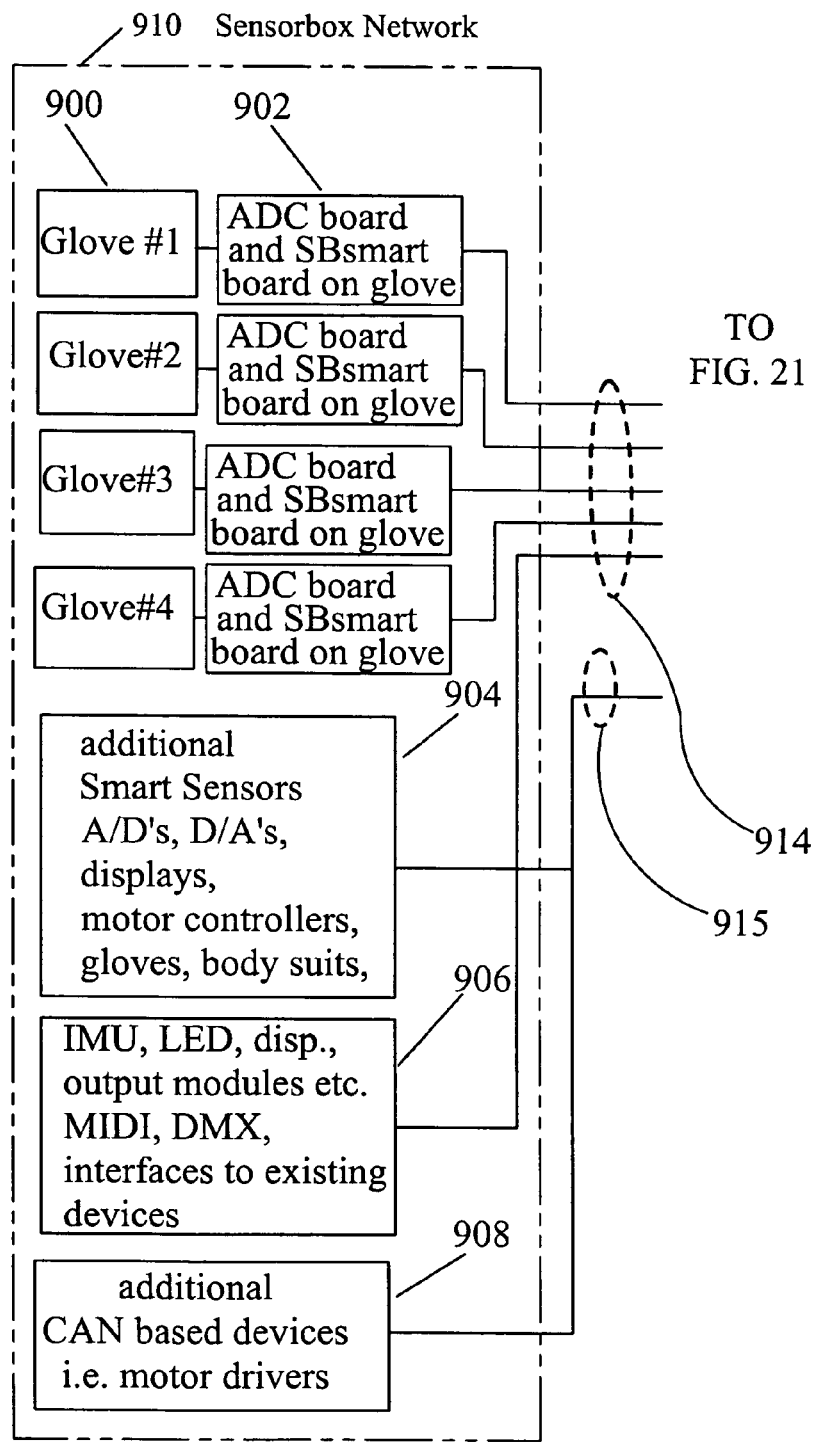
FIG. 20 is a block diagram showing signals leaving the sensor glove and traveling via a cable path to the KorRe Circuits of FIGS. 10a, 10b and 10c.
Figure 21:
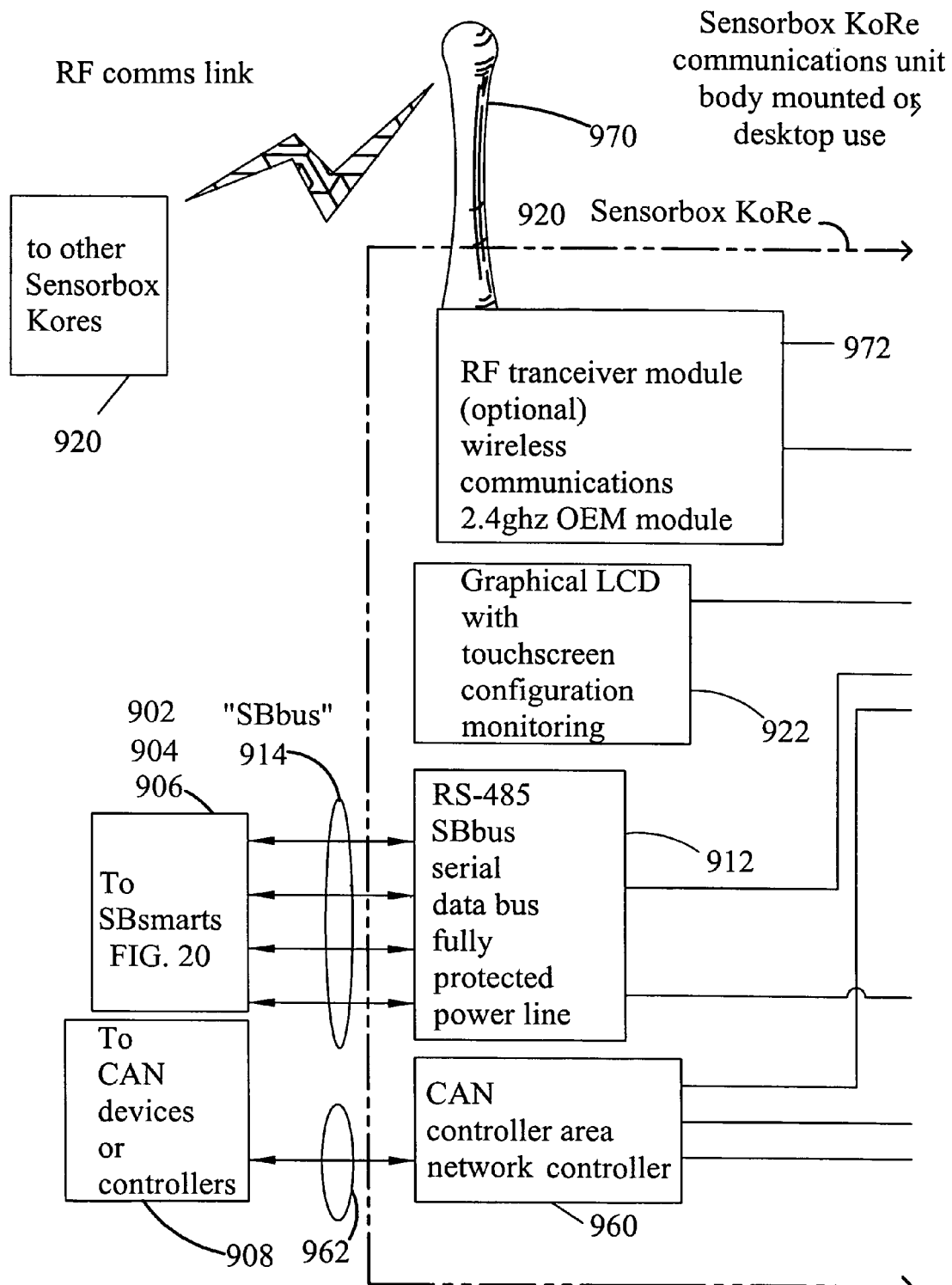
FIGS. 21, 22 and 23 are block diagrams that show the signal processing of digital signals leaving the sensor glove via a path from the block diagram of FIG. 20.

FIGS. 17, 18 and 19 are a block diagram of the SBsmart (800) circuit, as previously described from FIG. 7, is connected to the SBbus (914) via an RS-485 transceiver (912) with a high quality miniature push-pull latching LEMO connector (806) with a splitter board allowing additional SBsmart circuits, such as for inertial measurement (870), mounted directly on the glove, or to be daisy chained. Environmentally sealed LEMO connectors can be used to provide protection for use under harsh conditions.

A custom ADC board (810) connects three 8-channel 16-bit analog-to-digital converters (812) and associated signal conditioning/filtering components (814) to receive the sensor data from up to 24 sensors.

Analog sensors (880) comprising three potentiometers (6c, 6d, 6e) and a dual or triple axis accelerometer circuit (6k) are connected via wires to the ADC board (810).

Thin flexible circuit boards (852, 854) are mounted directly to the glove rigid reference base (2j) and connect potentiometers for each finger (78,856), signal conditioning (858), and a highly flexible/resilient flex cable (846) to connect to the flex sensor (840) mounted on a bend board (848) containing bend conditioning circuitry (844), a pivot point (841) attaching to the bell crank (56,842) that couples with the potentiometer's (78,856) gear.

The bend conditioning circuitry (844) conditions, amplifies, and converts the resistive flex sensors to a voltage before it gets filtered (814) and the sampled by the ADC (812).

Flex cables (850) are used as interconnects for the signals between the various circuit boards—allowing for circuits continuing down the side of the glove at 90 degrees to the top of the rigid reference base 42.

An acrylic rigid flap (170, 830) has a circuit board with signal conditioning (832) of the mounted force sensing resistors (FSR) (834) used to measure the touch pressure from 4 individual FSRs.

All the sensors on the glove can be sampled at very high speed on-board the SBsmart (800) allowing for various digital conditioning and analysis.

Feedback to the glove user is provided thru optional variable intensity LEDs (874), or via a graphical LCD or OLED display (872) mounted on the glove, allowing information sent from the application (941), PC host (940), or local/remote KoRe (920) to be displayed to provide local signal monitoring, configuration information, remote signal monitoring (inter-user signaling), timecode display, scene cues, etc.

Sensorbox System

FIGS. 20, 21, 22 and 23 gives an overview of the connections between the glove (900) and its on-board circuitry (902), the Sensorbox (920), the PC Host (940) and applications (941).

Each glove contains the necessary analog signal conditioning circuits along with a microprocessor, analog-to-digital conversion circuitry, and digital processing algorithms to produce the desired signals and transmit them via a small diameter cable along a serial data bus "SBbus" (914) to the Sensorbox communications unit "KoRe" (920). Multiple gloves and other SBsmart circuits can be connected to the same SBbus, as shown in FIG. 9, forming the Sensorbox Network (910).

The Sensorbox KoRe (920) is housed in a small rugged environmentally protected anodized extruded aluminum enclosure that can be worn on the body and used with an internal battery (991) and on-board radio-frequency transceiver (972) to communicate with other KoRes.

By constructing a sensor network on the body (910) connected to a wireless (970) Sensorbox KoRe, events can be synchronized between disparate input/output devices. Glove inputs (900) can be read by a body-mounted Sensorbox KoRe (920), transmitted wirelessly (970) to another KoRe controlling motors/lights (904) in an animatronic puppet, as well as to a KoRe connected to a PC host (940) sending data to 3D animation software (942) for controlling a virtual character.

Sensorbox KoRe:

FIG. 19, 20, 21 shows how the Sensorbox communications unit "KoRe" (920) connects the gloves (900) and their SBsmart (902) circuits on the Sensorbox Network (910) over the SBbus (914), and how data is communicated via a connection (930) to a PC host (940) and associated applications (941).

Figure 22:
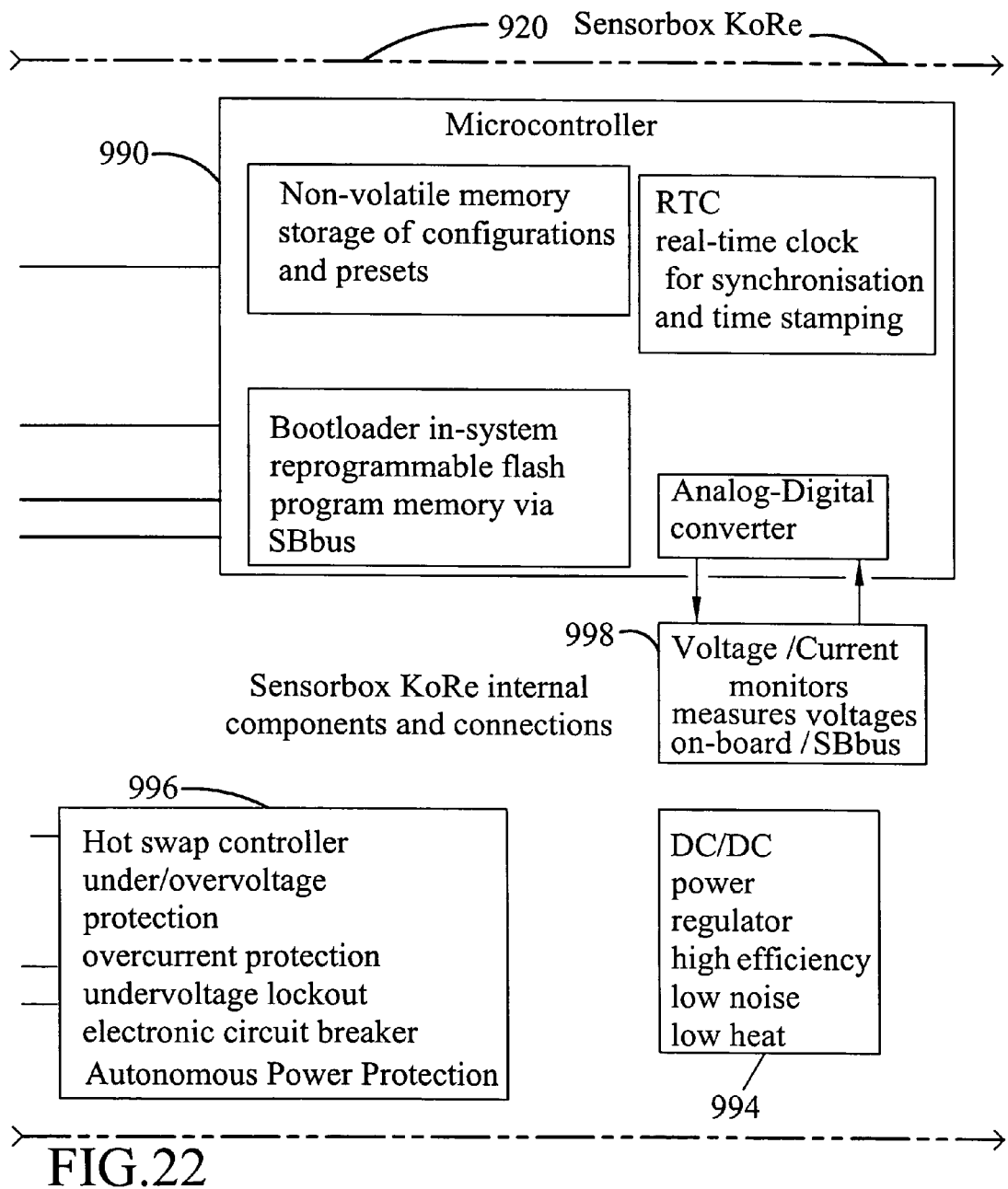
Figure 23:
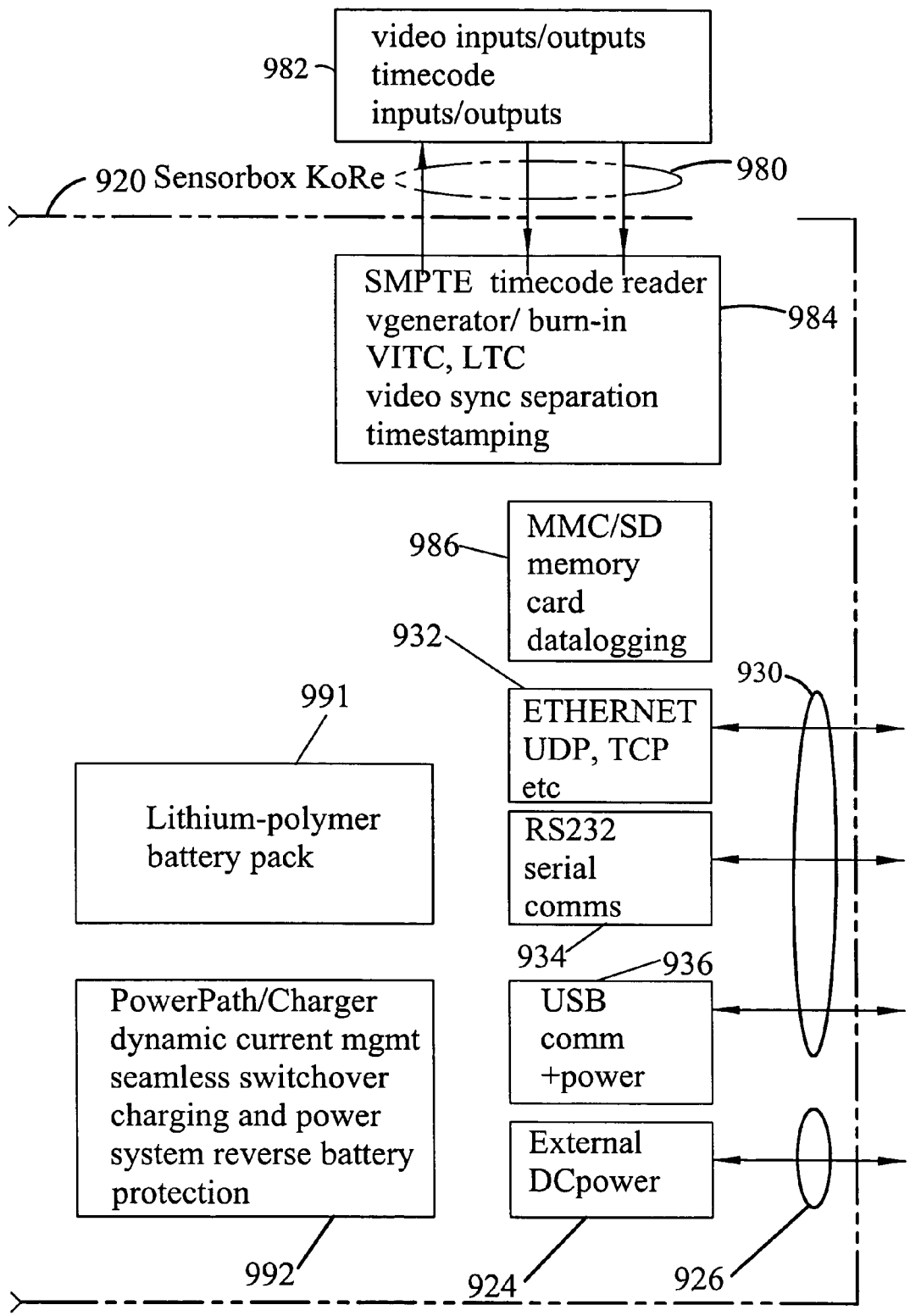

FIG. 22, 23 details the internal components and connections of the Sensorbox "KoRe" (920).

Power is provided to the KoRe from the external DC power (924) connection with a DC adapter or external battery pack, from an internal rechargeable Lithium-Polymer battery pack (991), or from power drawn on the USB bus (936). A power-path controller/charge management system (992) handles seamless switching from the different sources of power, charging of the battery, and reverse polarity protection. A high-efficiency DC/DC power regulator (994) provides regulated power with low heat and low noise.

The KoRe features autonomous power protection that monitors and protects the connections to the SBbus (914) with a hot swap controller (996) that forms an electronic circuit breaker capable of shutting down power to the SBbus quickly in the event of any fault condition without any intervention necessary from the on-board microcontroller (990). The SBbus power can also be switched on and off from the microcontroller (990).

Voltage and current monitors (998) are input to the on-board microcontroller's (990) analog-to-digital converter to keep track of power use both on-board and on the SBbus.

Data and power are transmitted on the SBbus (914) via a RS-485 transceiver (912) and using a proprietary protocol for a high-speed half-duplex multi-drop multi-master network. Alternately, an industry-standard CANbus (962) interface is provided via an on-board CAN controller and transceiver (960).

An on-board graphical LCD display with touchscreen (922) provides for configuration and monitoring of data, status, and settings.

To communicate to a PC host or remote device, several transports (930) can be used: Ethernet (932), RS-232 serial (934), or USB (936).

An optional wireless transceiver (972) allows for an RF communications link (970) to be established between remote KoRes. A high performance 2.4 GHz frequency hopping spread spectrum OEM transceiver provides low-latency high data rate robust multipoint communications, with strong interference rejection from existing RF noise from other devices.

A multimedia (MMC) or secure digital (SD) memory card (986) allows the KoRe to provide data-logging with time-stamping of the sensor data and playback capabilities. Real-time low-latency data can be sent to the PC Host (940) at the desired rate, while data sampled at a much higher rate can be stored on the card to playback or transfer later, ensuring optimal fidelity and minimizing transient, jitter, quantization or aliasing noise(s).

SMPTE timecode receiver/generator (984) circuitry provides signals (980) to/from external video equipment (982)— reading or generating timecode. The KoRe can send synchronize all the connected SBsmarts (902,904,906) or CAN devices (908) and timestamp their data.

Those skilled in the art will appreciate that various adaptations and modifications of the preferred embodiments can be configured without departing from the scope and spirit of the invention. Therefore, it is to be understood that the invention may be practiced other than as specifically described herein, within the scope of the appended claims.

What is claimed is:

1. A sensor glove worn on the fingers and hand of a performer, for providing analog signals representing the motion of one or more fingers in the glove, the sensor glove comprising:

a palmer region, and at least one finger region, the finger region being worn on a finger, the finger region being attached to the palmer region, the finger region and palmer region each having a corresponding palmer surface and a dorsal surface, a rigid reference base, the rigid reference base having a top surface and an underside, the rigid reference base underside being coupled to the dorsal surface of the palmer region, a mechanical link and means for coupling motion between the dorsal surface of the finger region and the rigid reference base to a control input for a pot to change the resistance of the pot in response to a bending motion of the finger in the finger region with respect to the rigid reference base, a mechanical link and means for translating a first and second degree of freedom motion of the thumb with respect to the rigid reference base into a thumb control signal, and a rigid flap, the rigid flap having an upper and lower surface, a first force sensitive resistor being coupled to the rigid flap upper surface, the rigid flap being pivotally coupled to the rigid reference base on a rotational axis transverse to the extended direction of a finger, the force sensitive resistor being positioned on the rigid flap upper surface at a location under the finger, the rigid flap lower side being supported or raised by motion of the thumb to permit the finger to provide a force to the first force sensitive resistor to change the resistance of the first force sensitive resistor in response to an increase in pressure between the thumb and the finger with the rigid flap and force sensitive resistor therebetween.

2. The sensor glove of claim 1 further comprising:

an index finger region for receiving the index finger, the sensor glove having a vertical motion sensing pot having a case coupled to the top of the rigid reference base and an input axis transverse to the longitudinal axis, the input axis of the vertical sensing pot being above the top surface of the rigid reference base, the vertical sensing pot input axis having a shaft with a bell crank there on, a link coupling the distal surface of the finger region of the index finger with an arm of the bell crank to provide rotational motion in a vertical plane to the input axis shaft in response to vertical motion of the top surface of the index finger region, and a horizontal motion sensing pot having a case coupled to a vertical flange, the vertical flange being integrally coupled to the top of the rigid reference base, the horizontal motion sensing pot having an input axis normal to the plane of the palmer region, the input axis of the horizontal sensing pot having a shaft with a bell crank there on, a link coupling the distal surface of the finger region of the index finger with an arm of the horizontal sensing pot bell crank to provide rotational motion in a horizontal plane to the input axis shaft in response to horizontal motion of the top surface of the index finger region.

3. The sensor glove of claim 1 further comprising:

means for independently sensing vertical motion of the thumb with respect to the top surface of the rigid reference base and means for independently sensing horizontal motion of the thumb with respect to the top surface of the rigid reference base further comprising:

a frame for mounting and holding a bearing rod in horizontal relation with the top surface of the rigid reference base, the bearing rod being positioned in substantially co-parallel relation and displaced to be on the thumb side of the top surface of the rigid reference base, a swing plate having a displaced bore for receiving the bearing rod, the swing plate being free to rotate on the bearing rod in a plane transverse to the longitudinal axis of the rigid reference base, the plate having a swing plate bearing with an axis normal to the plane of the swing plate, an L-bracket coupled to the swing plate by the swing plate bearing positioned in an upper region of the L-bracket, the lower region of the L-bracket being formed to extend in the direction of the thumb, the L-bracket being free to rotate on the swing plate bearing in the plane of the swing plate, the lower region of the L-bracket having a distal end positioned along the length of the thumb and a proximal end under the swing plate bearing a link of wire flexibly coupling the distal end of the L-bracket to the thumb finger region, the wire transferring motion of the thumb finger region in the vertical plane and in the horizontal plane to the distal end of the L-bracket, a thumb motion bell crank supported and free to pivot on the bearing rod, the thumb motion bell crank having a vertical pivot bore and a horizontal transfer bore, and a ball linkage rod having a ball linkage on a lower end coupled to the L-bracket and a ball linkage on an upper end coupled to the vertical pivot bore in the thumb motion bell crank.

4. The sensor glove of claim 1 further comprising:

at least one bend sensor, each bend sensor being mechanically coupled to the dorsal side of a finger region, each said bend sensor being positioned to be in close proximity to a sense location for providing a fine bend signal characterizing a bend motion of the glove finger region corresponding to the sense location.

5. A sensor glove worn on the fingers and hand of a performer, for providing analog signals representing the motion of one or more fingers in the glove, the sensor glove comprising:

a palmer region, and at least one finger region, the finger region being worn on a finger, the finger region being attached to the palmer region, the finger region and palmer region each having a corresponding palmer surface and a dorsal surface, a rigid reference base, the rigid reference base having a top surface and an underside, the rigid reference base underside being coupled to the dorsal surface of the palmer region, a mechanical link and means for coupling motion between the dorsal surface of the finger region and the rigid reference base to a control input for a pot to change the resistance of the pot in response to a bending motion of the finger in the finger region with respect to the rigid reference base, a mechanical link and means for translating a first and second degree of freedom motion of the thumb with respect to the rigid reference base into a thumb control signal, a rigid flap, the rigid flap having an upper and lower surface, a first force sensitive resistor being coupled to the rigid flap upper surface, the rigid flap being pivotally coupled to the rigid reference base on a rotational axis transverse to the extended direction of a finger, the force sensitive resistor being positioned on the rigid flap upper surface at a location under the finger, the rigid flap lower side being supported or raised by motion of the thumb to permit the finger to provide a force to the first force sensitive resistor to change the resistance of the first force sensitive resistor in response to an increase in pressure between the thumb and the finger with the rigid flap and force sensitive resistor therebetween, means for independently sensing vertical motion of the thumb with respect to the top surface of the rigid reference base and means for independently sensing horizontal motion of the thumb with respect to the top surface of the rigid reference base, and for providing a vertical thumb motion signal and a horizontal thumb motion signal to a signal conditioner.

6. A sensor glove worn on the fingers and hand of a performer, for providing analog signals representing the motion of one or more fingers in the glove, the sensor glove comprising:

a palmer region, and at least one finger region, the finger region being worn on a finger, the finger region being attached to the palmer region, the finger region and palmer region each having a corresponding palmer surface and a dorsal surface, a rigid reference base having a longitudinal axis extending from the palmer region to a wrist region, the wrist region extending to cover the base ends of the metacarpal bones rearward beyond and covering the scaphoid and lunate bones, the rigid reference base having a top surface and an underside, the rigid reference base underside being coupled to the dorsal surface of the palmer region, the rigid reference base covering the palmer region and having integral fight and left flanges extending downward below the dorsal surface of the palmer region covering the hand, and rearward to a proximal end terminating after the wrist region, a radial bar pivotally coupled to a first pivot axis transverse to and passing through the proximal end of the fight and left flanges of the rigid reference base, an arm plate having a longitudinal axis extending from a distal end pivotally coupled to the radial bar and a proximal end attached to the dorsal side of the glove, an accelerometer having at least a first sensitive axis, the accelerometer being coupled to the arm plate to provide at least a first acceleration signal corresponding to acceleration experienced along its first sensitive axis, the sensitive axis of the accelerometer being fixed to the longitudinal axis of the arm plate and the forearm, the sensitive axis of the accelerometer being substantially decoupled from rotation of the hand with respect to the forearm by operation of the pivot coupling at the distal end of the arm plate, and a rigid flap, the rigid flap having an upper and lower surface, a first force sensitive resistor being coupled to the rigid flap upper surface, the rigid flap being pivotally coupled to the rigid reference base on a rotational axis transverse to the extended direction of a finger, the force sensitive resistor being positioned on the rigid flap upper surface at a location under the finger, the rigid flap lower side being supported or raised by motion of the thumb to permit the finger to provide a force to the first force sensitive resistor to change the resistance of the first force sensitive resistor in response to an increase in pressure between the thumb and the finger with the rigid flap and force sensitive resistor therebetween.

7. The sensor glove of claim 6 further comprising:

means for independently sensing vertical and horizontal motion of the thumb with respect to the top surface of the rigid reference base and means for independently sensing horizontal motion of the thumb with respect to the top surface of the rigid reference base further comprising:

a frame for mounting and holding a bearing rod in horizontal relation with the top surface of the rigid reference base, the bearing rod being positioned in substantially co-parallel relation and displaced to be on the thumb side of the top surface of the rigid reference base, a swing plate having a displaced bore for receiving the bearing rod, the swing plate being free to rotate on the bearing rod in a plane transverse to the longitudinal axis of the rigid reference base, the plate having a swing plate bearing with an axis normal to the plane of the swing plate, an L-bracket coupled to the swing plate by the swing plate bearing positioned in an upper region of the L-bracket, the lower region of the L-bracket being formed to extend in the direction of the thumb, the L-bracket being free to rotate on the swing plate bearing in the plane of the swing plate, the lower region of the L-bracket having a distal end positioned along the length of the thumb and a proximal end under the swing plate bearing a link of wire flexibly coupling the distal end of the L-bracket to the thumb finger region, the wire transferring motion of the thumb finger region in the vertical plane and in the horizontal plane to the distal end of the L-bracket, a thumb motion bell crank supported and free to pivot on the bearing rod, the thumb motion bell crank having a vertical pivot bore and a horizontal transfer bore, and a ball linkage rod having a ball linkage on a lower end coupled to the L-bracket and a ball linkage on an upper end coupled to the vertical pivot bore in the thumb motion bell crank.

8. A sensor glove worn on the fingers and hand of a performer, for providing analog signals representing the motion of one or more fingers in the glove, the sensor glove comprising:

a palmer region, and at lease one finger region, the finger region being worn on a finger of the performer, the finger region being attached to the palmer region, the finger region and palmer region each having a corresponding palmer surface and a dorsal surface, a rigid reference base having a longitudinal axis extending from the palmer region to
a wrist region, the wrist region extending to cover the base ends of the metacarpal bones rearward beyond and covering the performer's scaphoid and lunate bones,
a rigid reference base having a top surface and an underside,
the rigid reference base underside being coupled to the dorsal surface of a palmer region of the rigid reference base covering the palmer region and having integral fight and left flanges extending downward below the dorsal surface of the hand, and rearward to a proximal end terminating after the wrist region,
a mechanical link means for independently translating a first and second degree of freedom motion of the thumb with respect to the rigid reference base into independent first and a second thumb control signals the mechanical link means further comprising:
a frame for mounting and holding a bearing rod in horizontal relation with the top surface of the rigid reference base, the bearing rod being positioned in substantially co-parallel relation and displaced to be on the thumb side of the top surface of the rigid reference base,
a swing plate having a displaced bore for receiving the bearing rod, the swing plate being free to rotate on the bearing rod in a plane transverse to the longitudinal axis of the rigid reference base, the plate having a swing plate bearing with an axis normal to the plane of the swing plate,
an L-bracket coupled to the swing plate by the swing plate bearing positioned in an upper region of the L-bracket, the lower region of the L-bracket being formed to extend in the direction of the thumb, the L-bracket being free to rotate on the swing plate bearing in the plane of the swing plate, the lower region of the L-bracket having a distal end positioned along the length of the thumb and a proximal end under the swing plate bearing
a link of wire flexibly coupling the distal end of the L-bracket to the thumb finger region, the wire transferring motion of the thumb finger region in the vertical plane and in the horizontal plane to the distal end of the L-bracket,
a thumb motion bell crank supported and free to pivot on the bearing rod, the thumb motion bell crank having a vertical pivot bore and a horizontal transfer bore, and
a ball linkage rod having a ball linkage on a lower end coupled to the L-bracket and a ball linkage on an upper end coupled to the vertical pivot bore in the thumb motion bell crank.

* * * * *